(12) United States Patent
Perfetti

(10) Patent No.: US 6,642,003 B2
(45) Date of Patent: Nov. 4, 2003

(54) HUMAN GLUCOSE-DEPENDENT INSULIN-SECRETING CELL LINE

(75) Inventor: Riccardo Perfetti, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 75 days.

(21) Appl. No.: 09/920,868

(22) Filed: Aug. 2, 2001

(65) Prior Publication Data

US 2003/0113300 A1 Jun. 19, 2003

(51) Int. Cl.$^7$ ................................................. C12Q 1/68
(52) U.S. Cl. ........................... 435/6; 435/458; 435/459; 435/461; 435/366
(58) Field of Search ........................... 435/6, 458, 459, 435/461, 366

(56) References Cited

U.S. PATENT DOCUMENTS

| | | |
|---|---|---|
| 4,935,000 A | 6/1990 | Dudek |
| 5,120,712 A | 6/1992 | Habener |
| 5,219,752 A | 6/1993 | Takazawa et al. |
| 5,397,706 A | 3/1995 | Correa et al. |
| 5,512,549 A | 4/1996 | Chen et al. |
| 5,530,023 A | 6/1996 | Korth |
| 5,545,618 A | 8/1996 | Buckley et al. |
| 5,574,008 A | 11/1996 | Johnson et al. |
| 5,587,309 A | 12/1996 | Rubin et al. |
| 5,595,722 A | 1/1997 | Grainger et al. |
| 5,614,492 A | 3/1997 | Habener |
| 5,631,224 A | 5/1997 | Efendic et al. |
| 5,654,267 A | 8/1997 | Vuori et al. |
| 5,665,864 A | 9/1997 | Quaranta et al. |
| 5,670,360 A | 9/1997 | Thorens |
| 5,705,483 A | 1/1998 | Galloway et al. |
| 5,723,333 A | 3/1998 | Levine et al. |
| 5,744,327 A | 4/1998 | Newgard |
| 5,747,325 A | 5/1998 | Newgard |
| 5,773,255 A | 6/1998 | Laurence et al. |
| 5,792,656 A | 8/1998 | Newgard |
| 5,804,421 A | 9/1998 | Vinik et al. |
| 5,811,266 A | 9/1998 | Newgard |
| 5,837,236 A | 11/1998 | Dlnsmore |
| 5,840,531 A | 11/1998 | Vinik et al. |
| 5,846,747 A | 12/1998 | Thorens et al. |
| 5,846,937 A | 12/1998 | Drucker |
| 5,849,493 A | 12/1998 | Montminy et al. |
| 5,854,292 A | 12/1998 | Ailhaud et al. |
| 5,858,973 A | 1/1999 | Habener et al. |
| 5,861,278 A | 1/1999 | Wong et al. |
| 5,863,555 A | 1/1999 | Heiber et al. |
| 5,880,261 A | 3/1999 | Waeber et al. |
| 5,888,705 A | 3/1999 | Rubin et al. |
| 5,895,785 A | 4/1999 | Korth |
| 5,902,577 A | 5/1999 | Asfari et al. |
| 5,928,942 A | 7/1999 | Brothers |
| 5,948,623 A | 9/1999 | Sosa-Pineda et al. |
| 5,958,909 A | 9/1999 | Habener |
| 5,961,972 A | 10/1999 | Dinsmore |
| 5,977,071 A | 11/1999 | Galloway et al. |
| 5,981,488 A | 11/1999 | Hoffmann |
| 5,993,799 A | 11/1999 | Newgard |
| 5,994,127 A | 11/1999 | Selden et al. |
| 6,001,647 A | 12/1999 | Peck et al. |
| 6,004,775 A | 12/1999 | Shimasaki et al. |
| 6,006,753 A | 12/1999 | Efendic |
| 6,048,724 A | 4/2000 | Selden et al. |
| 6,051,689 A | 4/2000 | Thorens |
| 6,071,697 A | 6/2000 | Sosa-Pineda et al. |
| 6,087,129 A | 7/2000 | Newgard et al. |
| 6,110,707 A | 8/2000 | Newgard et al. |
| 6,110,743 A | 8/2000 | Levine et al. |
| 6,114,599 A | 9/2000 | Efrat |
| 6,127,598 A | 10/2000 | German et al. |
| 6,132,708 A | 10/2000 | Grompe |
| 6,133,235 A | 10/2000 | Galloway et al. |
| 6,153,432 A | 11/2000 | Halvorsen et al. |
| 6,160,022 A | 12/2000 | Bergeron, Jr. |
| 6,162,907 A | 12/2000 | Habener |
| 6,210,960 B1 | 4/2001 | Habener et al. |
| 6,329,336 B1 | 12/2001 | Bridon et al. |
| 6,448,045 B1 * | 9/2002 | Levine et al. |

FOREIGN PATENT DOCUMENTS

| | | |
|---|---|---|
| WO | 0009666 | 8/1998 |
| WO | 0139784 | 12/1999 |
| WO | 0168108 | 3/2000 |

OTHER PUBLICATIONS

Hongxiang Hui et al., "Glucagon–Like Peptide 1 Induces Differentiation of Islet Duodenal Homeobox–1—Positive Pancreatic Ductal Cells Into Insulin–Secreting Cells," *Diabetes*, vol. 50, pp. 785–796 (Apr. 2001).

R. Ritzel et al., "Glucagon–Like Peptide 1 Increases SEcretory Burst Mass of Pulsatile Insulin Secretion in Patients with Type 2 Diabetes and Impaired Glucose Tolerance," *Diabetes*, vol. 50, pp. 776–784 (Apr. 2001).

Xiaolin Wang et al., "Glucagon–like peptide–1 Regulates the Beta Cell Transcription Factor, PDX–1, in Insulinoma cells," *Endocrinology*, vol. 140, No. 10, pp. 4904–4907 (1999).

A. Vinik et al., "Induction of Pancreatic Islet Neogenesis," *Hormone and Metabolic Research*, vol. 29, No. 6, pp. 255–322 (Jun. 1997).

(List continued on next page.)

*Primary Examiner*—James Ketter
(74) *Attorney, Agent, or Firm*—Pillsbury Winthrop LLP

(57) ABSTRACT

Disclosed herein is a novel cell line of human pancreatic cells that secrete insulin in a glucose-dependent manner. The cell line comprises pancreatic cells, such as PANC-1 cells, which are transfected so as to express IDX-1 and cultured in GLP-1. The cell line may be used to investigate the function and development of pancreatic cells, as well as to test the efficacy of drugs that stimulate insulin secretion.

30 Claims, 12 Drawing Sheets

(2 of 12 Drawing Sheet(s) Filed in Color)

OTHER PUBLICATIONS

KM Narayan et al., "Translation research for chronic disease: the case of diabetes," *Diabetes Care*, 23:1794–1798 (2000).

DJ Drucker, "The glucagon–like peptides," *Endocrinology*, 142:521–527 (2001).

B. Thorens and G. Waeber, "Glucagon–like peptide–I and the control of insulin secretion in the normal state and in NIDDM," *Diabetes*, 42:1219–1225 (1993).

MA Nauck et al., "Influence of glucagon–like peptide 1 on fasting glycemia in type 1 diabetic patients treated with insulin after sulfonylurea secondary failure," *Diabetes Care*, 21:1925–1931 (1998).

SY Shieh and MJ Tsai, "Cell–specific and ubiquitous factors are responsible for the enhancer activity of the rate insulin II gene," *J Biol Chem*, 266:16708–16714 (1991).

X. Wang et al., "Glucagon–like peptide–1 regulates the beta cell transcription factor, PDS–1, in insulinoma cells," *Endocrinology*, 140:4904–4907 (1999).

R. Perfetti and P. Merkel, "Glucagon–like peptide–1: a major regulator of pancreatic β–cell function," *European J Endocrinol*, 143:717–725 (2000).

A. Vinik et al., "Induction of pancreatic islet neogenesis," *Horm Metab Res (Symposium Report)*, 29:278–293 (1997).

MA Nauck et al., "Normalization of fasting hyperglycemia by exogenous glucagon–like peptide–1 [7–36 amide] in type 2 (non–insulin dependent) diabetic patients," *Diabetologia*, 36:741–744 (1993).

C. Orsakov, "Glucagon–like peptide–1, a new hormone of the enteroinsular axis," *Diabetologia*, 35:701–711 (1992).

JJ Holst, "Glucagon–like peptide–1 (GLP–1) a newly discovered GI hormone," *Gastroenterology*, 107:1848–1855 (1994).

MA Hussain and JF Habaner, "Glucagon–like peptide–1 increases glucose–dependent activity of the homeoprotein IDX–1 transactivating domain in pancreatic beta–cells," *Biochemical & Biophysical Research Communications*, 274:616–619 (2000).

CA Leech et al., "Expression of cAMP–regulated guanine nucleotide exchange factors in pancreatic beta–cells," *Biochemical & Biophysical Research Communication*, 278:44–47.

J. Buteau et al., "Glucagon–like peptide–1 promotes DNA synthesis, activates phosphatidylinositol 3–kinase and increases transcription factor pancreatic and duodental homebox gene 1 (PDX–1) DNA binding activity in beta (INS–1)–cells," *Diabetologia*, 42:856–864 (1999).

DA Stoffers et al., "Homeodomain protein IDX–1: A master regulator of pancreas development and insulin gene expression," *Trends Endocrinology Metab*, 8:145:151 (1997).

A. Wilmen et al., "The genomic organization of the human GLP–Receptor gene," *Exp Clin Endocrinol Diabetes*, 106:299–302 (1998).

G. Teitelman et al., "Cell lineage analysis of pancreatic islet cell development: glucagon and insulin cells arise from catecholaminergic precursor present in the pancreatic duct," *Dev Biol*, 121:454–466 (1987).

R. L. Pictet et al., "An ultrastructural analysis of the developing embryonic pancreas," *Dev Biol*, 29:436–467 (1972).

J. Jonsson et al., "Insulin–promotor factor 1 is required for pancreas development in mice," *Nature*, 371:606–609 (1994).

U. Ahlgren et al., "Independent requirement for ISL1 in formation of pancreatic mesenchyme and islet cells," *Nature*, 385:257–260 (1997).

F. J. Naya et al., "Diabetes, defective pancreatic morphogenesis, and abnormal enteroendocrine differentiation in BETA2/NeuroD–deficient mice," *Genes Dev*, 11:2323–2334 (1997).

A. Sosa–Pineda et al., "The Pax4 gene is essential for differntiation of insulin–producing beta cells in the mammalian pancreas," *Nature*, 386:399–402 (1997).

S. Bonner–Weir et al., "A second pathway for regeneration of adult exocrine and endocrine pancrease—A possible recapitulation of embryonic development," *Diabetes*, 42:1715–1720 (1993).

G. Xu et al., "Exendin–4 stimulates both beta–cell replication and neogenesis, resulting in increased beta–cell mass and improved glucose tolerance in diabetic rats," *Diabetes*, 48:2270–2276 (1999).

Y. Wang et al., "Glucagon–like peptide–1 can reverse the age–related decline in glucose tolerance in rats," *J Clin Invest*, 99:2883–2889 (1997).

E. Elstner et al., "Synergistic decrease of clonal proliferation, induction of differentiation and apoptosis of acute promyelocytic leukemia cells after combined treatment with novel 20–epi vitamin D3 analogs and 9–cis reinoid acid," *J Clin Invest*, 99:349–360 (1997).

D.J. Drucker et al., "Glucagon–like peptides," *Diabetes*, 47:159–169 (1998).

H. Kaneto et al., "Expression of heparin–binding epidermal growth factor–like growth factor during pancreas development; A potential role of PDX–1 in transcriptional activation," *J Biol Chem*, 272:29137–29143 (1997).

J.F. Habener et al., "A newly discovered role of transcription factors involved in pancreas developmentand the pathogenesis of diabetes mellitus," *Proc Assoc Am Phys*, 110:12–21 (1998).

L. Bouwens, "Transdifferentiation versus stem cell hypothesis for the regeneration of islet beta–cells in the pancrease," *Microscopy Research & Technique*, 43:332–336 (1998).

J.C. Jonas et al., "Chronic hyperglycemia triggers loss of pancreatic beta cell differentiation in an animal model of diabetes," *J Biol Chem*, 274:14112–14121 (1999).

D.T. Finegood et al., "Prior streptozotocin treatment does not inhibit pancreas regeneration after 90% pancreatectomy in rats," *Am J Physiol*, 276:E822–E827 (1999).

R.N. Wang et al., "Beta–cell growth in adolescent and adult rats treated with streptozotocin during the neonatal period," *Diabetologia*, 39:548–557 (1996).

A. Pick et al., "Role of apoptosis in failure of beta–cell mass compensation for insulin resistance and beta–cell defects in the male Zucker diabetic fatty rat," *Diabetes*, 47(3):358–64 (1998).

V.K. Ramiya et al., "Reversal of insulin–dependent diabetes using islets generated in vitro from pancreatic stem cells," *Nature Medicine*, 6(3):278–282 (2000).

S. Bonner–Weir et al., "In vitro cultivation of human islets from expanded ductal tissue," *Proc. Natl. Aca. Sci USA*, 97(14):7999–8004.

H. Hui et al., "GLP–1 Induces Differentiation of IDX–1 Positive Pancreatic Ductal Cells into Insulin Secreting Cells," *The Endocrine Society's 82nd Annual Meeting, Program & Abstracts* (Jun., 2000).

C. Widmann et al., "Desensitization and phosphorylation of the glucagon–like peptide–1 (GLP–1 receptor by GLP–1 and 4–phorbol 12–myristate 13–acetate," *J. Molecular Endocrinology* 10(1):62–75 (1996).

* cited by examiner

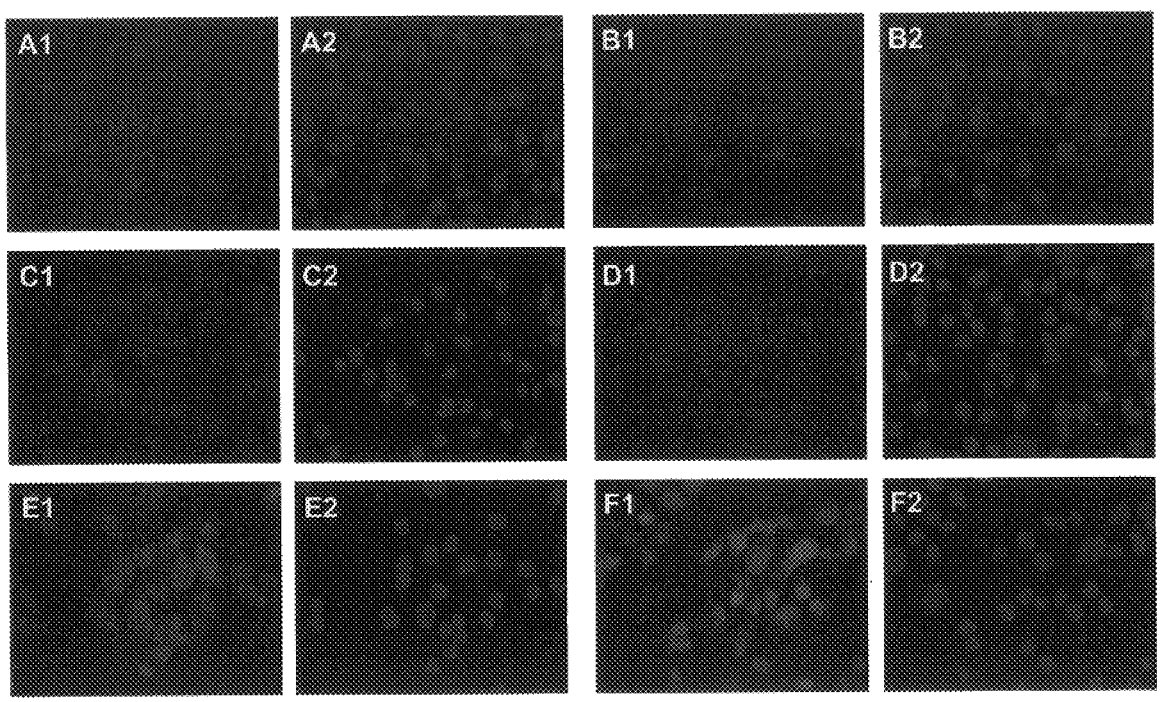
FIG. 3A-F

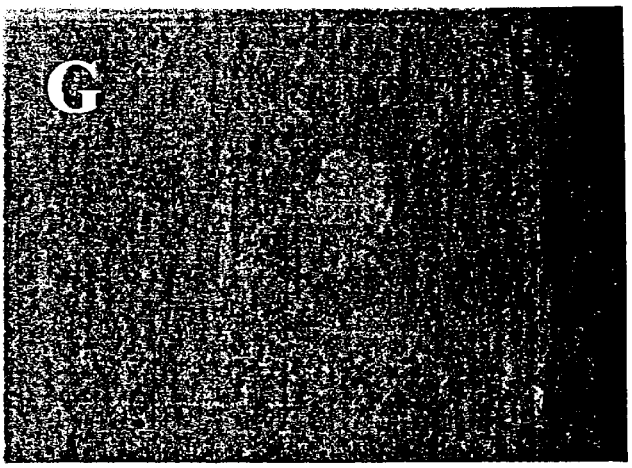
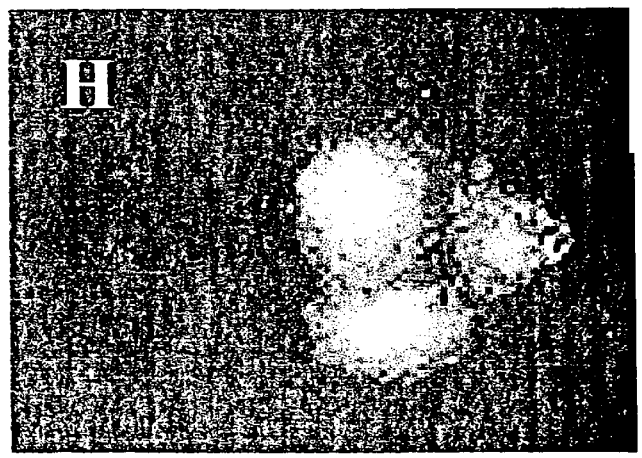
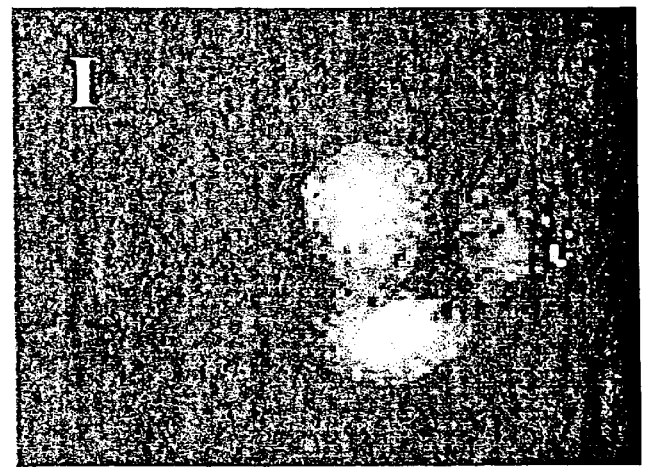
FIG. 3 (continued)

ARIP
A 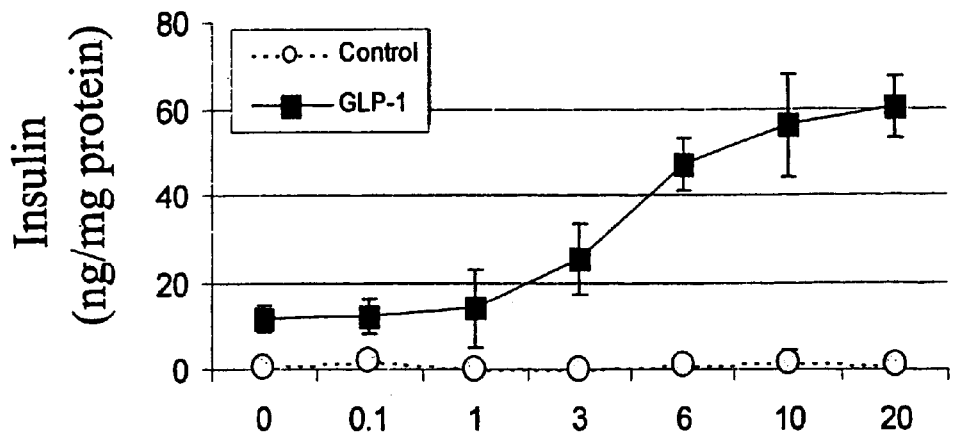
PANC-1
B 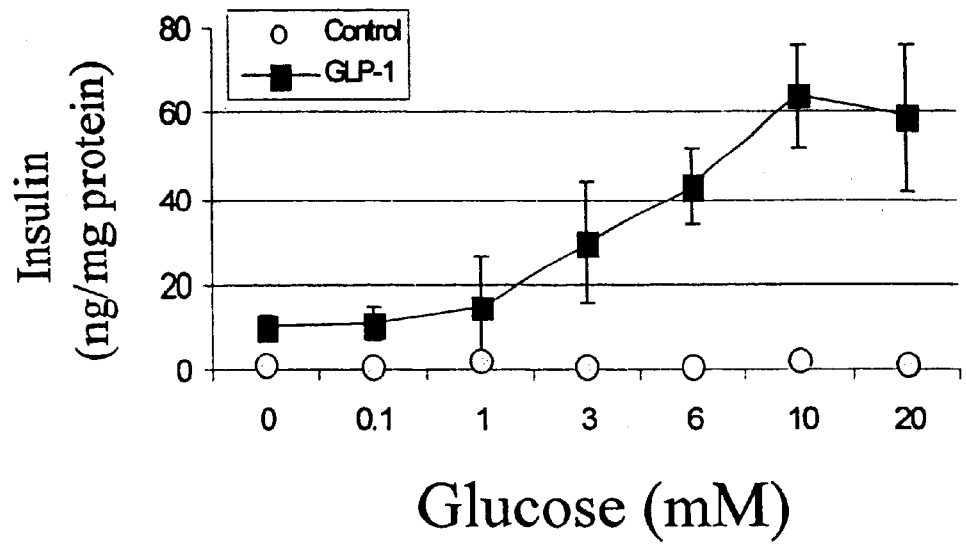
FIG. 6

```
GAATTCCGGGGCGCTGAGAGTCCGTGAGCTGCCCAGCGCCTAAGGCCTGGCTTGTAGCTCC   61

M  N  S  E  E  Q  Y  Y    8
CTACCCCGGGCTGCCGGCCCCGAAGTGCCGGCTGCCACCATGAATAGTGAGGAGCAGTACT  122

A  A  T  Q  L  Y  K  D  P  C  A  F  Q  R  G  P  V  P  E  F   28
ACGCGGCCACACAGCTCTACAAGGACCCGTGCGCATTCCAGAGGGGTCCGGTGCCAGAGTT  183

S  A  N  P  P  A  C  L  Y  M  G  R  Q  P  P  P  P  P  T  P   49
CAGTGCTAATCCCCCTGCGTGCCTGTACATGGGCCGCCAGCCCCCACCTCCGCCGACACCC  244

Q  F  A  G  S  L  G  T  L  E  Q  G  S  P  P  D  I  S  P  Y  E   69
CAGTTTGCAGGCTCGCTGGGAACGCTGGAACAGGGAAGTCCCCCGGACATCTCCCCATACG  305

V  P  P  L  A  D  D  P  A  G  A  H  L  H  H  L  P  A  Q    89
AAGTGCCCCCGCTCGCCGATGACCCGGCTGGCGCGCACCTCCACCACCACCTCCCAGCTCA  366

L  G  L  A  H  P  P  P  G  P  F  P  N  G  T  E  T  G  G  L   110
GCTCGGGCTCGCCCATCCACCTCCCGGACCTTTCCCGAATGGAACCGAGACTGGGGGCCTG  427

E  E  P  S  R  V  H  L  P  F  P  W  M  K  S  T  K  A  H  A  W  130
GAAGAGCCCAGCCGCGTTCATCTCCCTTTCCCGTGGATGAAATCCACCAAAGCTCACGCGT  488

K  S  Q  W  A  G  G  A  Y  A  A  E  P  E  E  N  K  R  T  R  150
GGAAAAGCCAGTGGGCAGGAGGTGCATACGCAGCAGAACCGGAGGAGAATAAGAGGACCCG  549

T  A  Y  T  R  A  Q  L  L  E  L  E  K  E  F  L  F  N  K  Y   171
TACAGCCTACACTCGGGCCCAGCTGCTGGAGCTGGAGAAGGAATTCTTATTTAACAAATAC  610

I  S  R  P  R  R  V  E  L  A  V  M  L  N  L  T  E  R  H  I  K  191
ATCTCCCGGCCTCGCCGGGTGGAGCTGGCAGTGATGCTCAACTTGACTGAGAGACACATCA  671

I  W  F  Q  N  R  R  M  K  W  K  K  E  D  K  K  R  S  S   211
AAATCTGGTTCCAAAACCGTCGCATGAAGTGGAAGAAAGAGGAAGATAAGAAACGTAGTAG  732

G  T  T  S  G  G  G  G  E  E  P  E  Q  D  C  A  V  T  S   232
CGGGACAACGAGCGGGGGCGGTGGGGGCGAAGAGCCGGAGCAGGATTGTGCCGTAACCTCG  793

G  E  E  L  L  A  L  P  K  P  P  P  P  G  G  V  V  P  S  G  V  252
GGCGAGGAGCTGCTGGCATTGCCAAAGCCACCACCTCCCGGAGGTGTTGTGCCCTCAGGCG  854

P  A  A  A  R  E  G  R  L  P  S  G  L  S  A  S  P  Q  P  S  272
TCCCTGCTGCTGCCCGGGAGGGCCGACTGCCTTCCGGCCTTAGTGCGTCCCCACAGCCCTC  915

283
   S  I  A  P  L  R  P  Q  E  P  R  *
CAGCATCGCGCCACTGCGACCGCAGGAACCCCGGTGAGGACCGCAGGCTGAGGGTGAGCGG  976

GTCTGGGACCCAGAGTGCGGACATGGGCATGGGCCCGGGCAGCTGGATAAGGGAGGGGATC 1037
ATGAGGCTTAACCTAAACGCCACACACAAGGAGAACATTCTTCTTGGGGGCACAAGAGCCA 1098
GTTGGGTATACCAGCGAGATGCTGGCAGACCTCTGGGAAAAAAAAGACCCGAGCTTCTGA  1159
AAACTTTGAGGCTGCCTCTCGTGCCATGTGAACCGCCAGGTCTGCCTCTGGGACTCTTTCC 1220
TGGGACCAATTTAGAGAATCAGGCTCCCAACTGAGGACAATGAAAAGGTTACAAACTTGAG 1281
CGGTCCCATAACAGCCACCAGGCGAGCTGGACCGGGTGCCTTTGACTGGTCGGCCGAGCAA 1342
TCTAAGGTTGAGAATAAAGGGAGCTGTTTGAGGTTTCAAAAAAAAAAAAAAACCGGAATTC 1404
```

FIG. 11

```
                              SEQUENCE LISTING

<160> NUMBER OF SEQ ID NOS: 21

<210> SEQ ID NO 1
<211> LENGTH: 1403
<212> TYPE: DNA
<213> ORGANISM: Rat

<400> SEQUENCE: 1
gaattccggg gcgctgagag tccgtgagct gcccagcgcc taaggcctgg cttgtagctc      60
cctaccccgg gctgccggcc ccgaagtgcc ggctgccacc atgaatagtg aggagcagta     120
ctacgcggcc acacagctct acaaggaccc gtgcgcattc cagagggtc cggtgccaga      180 gttcagtgct aatcccctg cgtgcctgta catgggccgc cagcccccac ctccgccgac      240
accccagttt gcaggctcgc tgggaacgct ggaacaggga agtccccgg acatctcccc      300 atacgaagtg ccccgctcg ccgatgaccc ggctggcgcg cacctccacc accacctccc      360
agctcagctc gggctcgccc atccacctcc cggacctttc ccgaatggaa ccgagactgg     420
gggcctggaa gagcccagcc gcgttcatct ccctttcccg tggatgaaat ccaccaaagc     480
tcacgcgtgg aaaagccagt gggcaggagg tgcatacgca gcagaaccgg aggagaataa     540
gaggacccgt acagcctaca ctcgggccca gctgctggag ctgagaagg aattcttatt      600 taacaaatac atctcccggc ctcgccgggt ggagctggca gtgatgctca acttgactga     660
gagacacatc aaaatctggt tccaaaaccg tcgcatgaag tggaagaaag aggaagataa     720
gaaacgtagt agcgggacaa cgagcggggg cggtgggggc gaagagccgg agcaggattg     780
tgccgtaacc tcgggcgagg agctgctggc attgccaaag ccaccacctc ccggaggtgt     840
tgtgccctca ggcgtccctg ctgctgcccg ggagggccga ctgccttccg gccttagtgc     900
gtccccacag ccctccagca tcgcgccact gcgaccgcag gaacccggt gaggaccgca     960 ggctgagggt gagcgggtct gggacccaga gtgcggacat gggcatgggc ccgggcagct    1020
ggataaggga ggggatcatg aggcttaacc taaacgccac acacaaggag aacattcttc    1080
ttgggggcac aagagccagt tgggtatacc agcgagatgc tggcagacct ctgggaaaaa    1140
aaaagacccg agcttctgaa aactttgagg ctgcctctcg tgccatgtga accgccaggt    1200
ctgcctctgg gactcttttcc tgggaccaat ttagagaatc aggctcccaa ctgaggacaa    1260
tgaaaaggtt acaaacttga gcggtcccat aacagccacc aggcgagctg gaccgggtgc    1320
ctttgactgg tcggccgagc aatctaaggt tgagaataaa gggagctgtt tgaggtttca    1380
aaaaaaaaaa aaaaccggaa ttc                                            1403

<210> SEQ ID NO 2
<211> LENGTH: 20
<212> TYPE: DNA
<213> ORGANISM: Rat

<400> SEQUENCE: 2
cctgcccagg cttttgtcaa                                                  20

<210> SEQ ID NO 3
<211> LENGTH: 19
<212> TYPE: DNA
<213> ORGANISM: Rat
```

<400> SEQUENCE: 3
ctccagtgcc aagtctgaa                                              19

<210> SEQ ID NO 4
<211> LENGTH: 20
<212> TYPE: DNA
<213> ORGANISM: Rat

<400> SEQUENCE: 4
ttagcaactg ggtctgcaat                                             20

<210> SEQ ID NO 5
<211> LENGTH: 20
<212> TYPE: DNA
<213> ORGANISM: Rat

<400> SEQUENCE: 5
ggtgtagtcc tacactcatg                                             20

<210> SEQ ID NO 6
<211> LENGTH: 20
<212> TYPE: DNA
<213> ORGANISM: Rat

<400> SEQUENCE: 6
aagggaacaa catcgtagga                                             20

<210> SEQ ID NO 7
<211> LENGTH: 20
<212> TYPE: DNA
<213> ORGANISM: Rat

<400> SEQUENCE: 7
cattggcggt cttcatagta                                             20

<210> SEQ ID NO 8
<211> LENGTH: 20
<212> TYPE: DNA
<213> ORGANISM: Rat

<400> SEQUENCE: 8
cgtaaagacc tctatgccaa                                             20

<210> SEQ ID NO 9
<211> LENGTH: 20
<212> TYPE: DNA
<213> ORGANISM: Rat

<400> SEQUENCE: 9
agccatgcca aatgtctcat                                             20

<210> SEQ ID NO 10
<211> LENGTH: 20
<212> TYPE: DNA
<213> ORGANISM: Rat

<400> SEQUENCE: 10
tctcttctgc aaccgaacct                                             20

<210> SEQ ID NO 11
<211> LENGTH: 20
<212> TYPE: DNA

<213> ORGANISM: Rat

<400> SEQUENCE: 11
ctggtgcagt gcaagtgtct         20

<210> SEQ ID NO 12
<211> LENGTH: 20
<212> TYPE: DNA
<213> ORGANISM: Human

<400> SEQUENCE: 12
ctcacacctg gtggaagctc         20

<210> SEQ ID NO 13
<211> LENGTH: 20
<212> TYPE: DNA
<213> ORGANISM: Human

<400> SEQUENCE: 13
agagggagca gatgctggta         20

<210> SEQ ID NO 14
<211> LENGTH: 20
<212> TYPE: DNA
<213> ORGANISM: Human

<400> SEQUENCE: 14
agctttgcag ttggtggaat         20

<210> SEQ ID NO 15
<211> LENGTH: 20
<212> TYPE: DNA
<213> ORGANISM: Human

<400> SEQUENCE: 15
aataagaatg cccgtgacga         20

<210> SEQ ID NO 16
<211> LENGTH: 21
<212> TYPE: DNA
<213> ORGANISM: Human

<400> SEQUENCE: 16
tggaccaagg cttcaaggcc g         21

<210> SEQ ID NO 17
<211> LENGTH: 21
<212> TYPE: DNA
<213> ORGANISM: Human

<400> SEQUENCE: 17
catgtagcag gcattgcagc c         21

<210> SEQ ID NO 18
<211> LENGTH: 20
<212> TYPE: DNA
<213> ORGANISM: Human

<400> SEQUENCE: 18
gtggggcgcc ccaggcacca         20

<210> SEQ ID NO 19
<211> LENGTH: 24

-continued

```
<212> TYPE: DNA
<213> ORGANISM: Human

<400> SEQUENCE: 19
ctccttaatg tcacgcacga tttc                                              24

<210> SEQ ID NO 20
<211> LENGTH: 20
<212> TYPE: DNA
<213> ORGANISM: Human

<400> SEQUENCE: 20
gtgtggcggc caattactac                                                   20

<210> SEQ ID NO 21
<211> LENGTH: 20
<212> TYPE: DNA
<213> ORGANISM: Human

<400> SEQUENCE: 21
cttggcaagt ctgcatttga                                                   20
```

HUMAN GLUCOSE-DEPENDENT INSULIN-SECRETING CELL LINE

FIELD OF THE INVENTION

Embodiments of the present invention are directed to a human pancreatic cell line transfected so as to express β-cell differentiation factor IDX-1. Cells so transfected respond to glucagon-like peptide-1 by differentiating into insulin-secreting β cells.

Embodiments of the present invention are directed to a human pancreatic cell line transfected so as to express β-cell differentiation factor IDX-1. Cells so transfected respond to glucogon-like/peptide-1 by differentiating into insulin-secreting βcells.

BACKGROUND OF THE INVENTION

Insulin is essential for proper metabolism in humans: in addition to its familiar role as the chief regulator of blood sugar levels in humans, it is essential for carbohydrate, lipid, and protein metabolism, as well. Pancreatic beta (β) cells of the islets of Langerhans, epithelial cells dispersed throughout the pancreas, secrete insulin. When β cells are destroyed or their function impaired, insulin production declines, and diabetes results.

The most common form of diabetes, presenting in nearly a million new cases every year in the United States, is type II diabetes. Type II refers to a group of disorders characterized by high blood levels of glucose (hyperglycemia) and a resistance to insulin. Administering insulin to such patients tends not to produce its usual effect: in healthy individuals, insulin increases glucose uptake by skeletal muscle and decreases glucose production in the liver; in individuals with type II diabetes, insulin tends not to do so. Many patients with type II diabetes, therefore, do not respond well to insulin therapy, even when it is administered at high doses.

Drugs that promote insulin secretion or that lower glucose levels by other means are commonly prescribed to treat patients with type II diabetes. Sulfonylureas are the principal drugs prescribed to such patients. They stimulate insulin production by directly stimulating β cells; the effectiveness of such drugs therefore depends on the number of functioning β cells remaining in the pancreas. Repaglinide also stimulates insulin production by stimulating β cells, but differs structurally from the sulfonylureas. Other drugs, such as troglitazone (known better by its brand name, REZULIN®) and metformin, lower glucose levels by reducing glucose production in the liver and by promoting insulin sensitivity. Another drug, acarbose, inhibits digestive enzyme secretion and thereby delays digestion of carbohydrates (which when broken down in the body ultimately yield glucose). The efficacy of these drugs is tested first in vitro using existing cell lines that seek to model insulin-secreting β cells. None of these cell lines provides a satisfactory model, however, because they lose their responsiveness to glucose. As a result, in vitro studies of insulin-secreting drugs currently provide only limited information regarding their efficacy.

Understanding the function and development of insulin-secreting β cells is a critical step in developing better drugs to treat—and ultimately cure—diabetes. Pancreatic endocrine and exocrine cells (the cells that secrete insulin and other hormones) originate from a precursor epithelial cell during the development of the pancreas. G. Teitelman and J. K. Lee, "Cell lineage analysis of pancreatic islet cell development: glucagon and insulin cells arise from catecholarnin-ergic precursor present in the pancreatic duct." *Dev. Biol.* 121:454–466, 1987; R. L. Pictet, W. R. Clark, R. H. Williams, and W. J. Rutter, "An ultrastructual analysis of the developing embryonic pancreas." *Dev. Biol.* 29:436–467, 1972 (the foregoing publications, and all other publications cited herein, are incorporated by reference in their entirety). Various differentiation factors are required to achieve the mature phenotype characteristic of islet beta β-cells.

New β-cells are formed from existing islets and from ductal epithelial cells. The latter source has greater intrinsic biological relevance. Indeed, the possibility of differentiating insulin-secreting cells from non-endocrine cells supports the hypothesis that the biological source (pancreatic ductal epithelium) for this compensatory mechanism may be present even in the setting of a generalized destruction of the entire population of islet β-cells. This is strongly supported by recent studies demonstrating that primary cultures of epithelial ductal cells (from human and mouse pancreas) are susceptible to undergo differentiation into endocrine cells. V. K. Ramiya, M. Maraist, K. E. Arfors, D. A. Schatz, A. E. Peck, J. G. Conmelius, "Reversal of insulin-dependent diabetes using islets generated in vitro from pancreatic stem cells." *Nature Medicine*, 6(3):278–82, 2000; S. Bonner-Weir, M. Taneja, G. C. Weir, K. Tatarkiewicz, K. H. Song, A. Sharma, J. J. O'Neil, "In vitro cultivation of human islets from expanded ductal tissue. *Proc. Natl. Aca. Sci. USA*, 14:7999–8004, 1997.

Growth and differentiation of islet β-cells is not limited to the embryological state. A constant remodeling of size and function of the islets of Langerhans occurs during the entire life of individuals and is likely to play an essential role in the prevention of diabetes. In adult rats, two independent pathways are utilized for the proliferation of pancreatic endocrine cells: in the first pathway of proliferation, new endocrine cells arise from the division and differentiation of cells within the islets; in the second pathway, the islets cells originate from precursor cells located in the pancreatic ductal epithelium. S. Bonner-Weir, L. A. Baxter, G. T. Schuppin, F. E. Smith, "A second pathway for regeneration of adult exocrine and endocrine pancreas. A possible recapitulation of embryonic development." *Diabetes* 42:1715–1720, 1993.

It has yet to be determined whether in the normal ductal epithelium there are different populations of cells, some of which are capable of differentiating into endocrine cells, while others have merely a structural role in defining the epithelial wall It is also possible that all pancreatic ductal epithelial cells could represent a not-fully-differentiated population of cells capable of acquiring a new phenotype Under specific stimuli, but this, too, has yet to be determined; at present, this possibility is a matter of speculation. It is likely that a coordinated activation of multiple differentiation factors, in a fashion similar to the sequence of events occurring during fetal development, is required for the cellular growth of the endocrine pancreas of adults. The mechanism (or mechanisms) for the activation of such a complex regulatory network in adulthood is poorly understood.

An incretin hormone, glucagon-like-peptide-1 (GLP-1), is believed to play a role in the development of the pancreas, though researchers have disagreed as to precisely what this role is. A decade ago, for example, U.S. Pat. No. 5,120,712, the entirety of which is incorporated by reference, stated that "The failure to identify any physiological role for GLP-1 caused some investigators to question whether GLP-1 was in fact a hormone and whether the relatedness between glucagon and GLP-1 might be artifactual." Researchers have more recently learned that GLP-1 has a function in rats. Bonner-Weir et al., for example, demonstrated that an analog of the incretin hormone glucagon-like-peptide-1 (GLP-1), termed exendin4, was able to increase islet mass in adult animals previously subjected to subtotal pancreatectomy. G. Xu, D. A. Stoffers, J. F. Habener, S. Bonner-Weir, "Exendin-4 stimulates both beta-cell replication and neogenesis, resulting in increased beta-cell mass and improved glucose tolerance in diabetic rats." *Diabetes* 48:2270–2276, 1999. Similarly, the inventor has demonstrated that treating glucose-intolerant aging Wistar rats with GLP-1 restored normal glucose tolerance and induced islet cell proliferation. Y. Wang, R. Perfetti, N. H. Greig, H. W. Holloway, K. A. DeOre, C. Montrose-Rafizadeh, D. Elahi, J. M. Egan, "Glucagon-like peptide-1 can reverse the age-related decline in glucose tolerance in rats." *J Clin Invest* 99:2883–2889, 1997.

Islet duodenal homeobox-1 ("IDX-1," also known variously as IPF-1/STF-1 and PDX-1) is a homeodomain protein and an insulin gene transcription factor expressed in the early pancreatic gland of the embryo. During pancreatic islet development, IDX-1 plays an important role in determining islet cell differentiation. It is the early IDX-1 gene expression during embryogenesis, coupled with the activation of other transcription factors (for example, NeuroDBeta 2, Pax 4, etc.), that determine the pancreatic endocrine hormone production. In adult (mature) animals, the expression of IDX-1 is repressed in the majority of pancreatic cells, with the exception of the β- and δ-cells (somatostatin-secreting cells) of the islets of Langerhans.

IDX-1 plays an important role in the development and functioning of the pancreas, though researchers have yet to elucidate precisely what that role is. Mice lacking islet IDX-1, for example, fail to develop a pancreas. J. Jonsson, L. Carlsson, T. Edlund, and H. Edlund, "Insulin-promoter factor 1 is required for pancreas development in mice. *Nature* 371:606–609, 1994. Islet-1, a LIM homeodomain-containing protein, is necessary for the development of the dorsal pancreas and is required for the generation of islet cells. U. Ahigren, S. L. Pfaff, T. M. Jessell, T. Edlund, and H. Edlund, "Independent requirement for ISL1 in formation of pancreatic mesenchyme and islet cells." *Nature* 385:257–260, 1997. Inactivation of BETA2/NeuroD or Pax4 genes cause a striking reduction in the number of insulin-producing cells and a failure to develop mature islets. F. J. Naya, H. P. Huang, Y. Qiu, H. Mutoh, F. J. DeMayo, A. B. Leiter, M. J. Tsai: "Diabetes, defective pancreatic morphogenesis, and abnormal enteroendocrine differentiation in BETA2/NeuroD-deficient mice." *Genes. Dev.* 11:2323–2334, 1997.

The mechanisms regulating proliferation and differentiation of the pancreatic hormone-producing cells and the chronology of these biological events are still largely undetermined. The sequence of events described herein suggests that the ability of regulating glucose uptake by the islet-specific glucose transporter GLUT2 is the first step necessary for the "sensitization" of the regulatory region(s) of the insulin gene to glucose. This would then promote the transcription of insulin mRNA. GLP-1-dependent activation of IDX-1 would further commit these cells to a β-cell-like pathway of differentiation by inducing the synthesis of glucokinase, the chief element of the glucose-sensing machinery of the islets of Langerhans.

Researchers have learned much of the role of GLP-1 and IDX-1 in the rat and mouse, where knock-out mouse or other animal models are available to study the role of these hormones. Researchers know little of the role GLP-1 and IDX-1 in the development of human insulin-secreting cells, or of their interaction with other hormones present in the endocrine system. There is therefore an important need in the art for an analytical tool that permits researchers to elucidate the role of GLP-1 and IDX-1 in humans. A human model would be of immense importance in testing theories of endocrine development, in evaluating antidiabetic drugs, and developing new approaches to treat diabetes.

SUMMARY OF THE INVENTION

It is an object of the invention to provide a model and analytical tool to study human insulin-secreting cells. It is a further object of the invention to provide an analytical tool that elucidates the role of GLP-1 and IDX-1—two hormones whose roles are incompletely understood in the development and functioning of human insulin secreting cells. It is a still further object of the invention to provide a human model that permits one to test theories of endocrine development, to evaluate antidiabetic drugs, and to develop new approaches to treat diabetes.

Disclosed herein is a novel insulin-secreting human cell line. The cell line of the invention is based on the surprising discovery that human pancreatic cells, when transfected with IDX-1 and cultured in GLP-1, differentiate into insulin-secreting β cells. These cells moreover behave in many respects as human β cells do in vivo. In a significant respect, these cells secrete insulin in a dose-dependent manner; that is, the more glucose these cells are exposed to, the more insulin they secrete. This important feature regarding this cell line makes it an ideal model to test antidiabetic drugs, such as sulfonylureas, repaglinide, and other drugs, that are commonly administered to patients with type II diabetes.

To date, no one has succeeded in constructing a cell line comprising human cells that secrete insulin in a dose-dependent manner. Such a cell line, disclosed for the first time herein, provides an important tool for investigating the function of the endocrine system, its development, and drugs that can affect it.

BRIEF DESCRIPTION OF THE FIGURES

The file of this patent contains at least one drawing executed in color. Copies of this patent with color drawings will be provided by the Office upon request and payment of the necessary fee.

FIGS. 1A and 1B show ARIP cells cultured with vehicle (FIG. 1A) or with medium containing GLP-1 (FIG. 1B). FIGS. 1E and F show PANC-1 cells cultured in the absence (FIG. 1C) or in the presence (FIG. 1D) of GLP-1.

Figure 2:
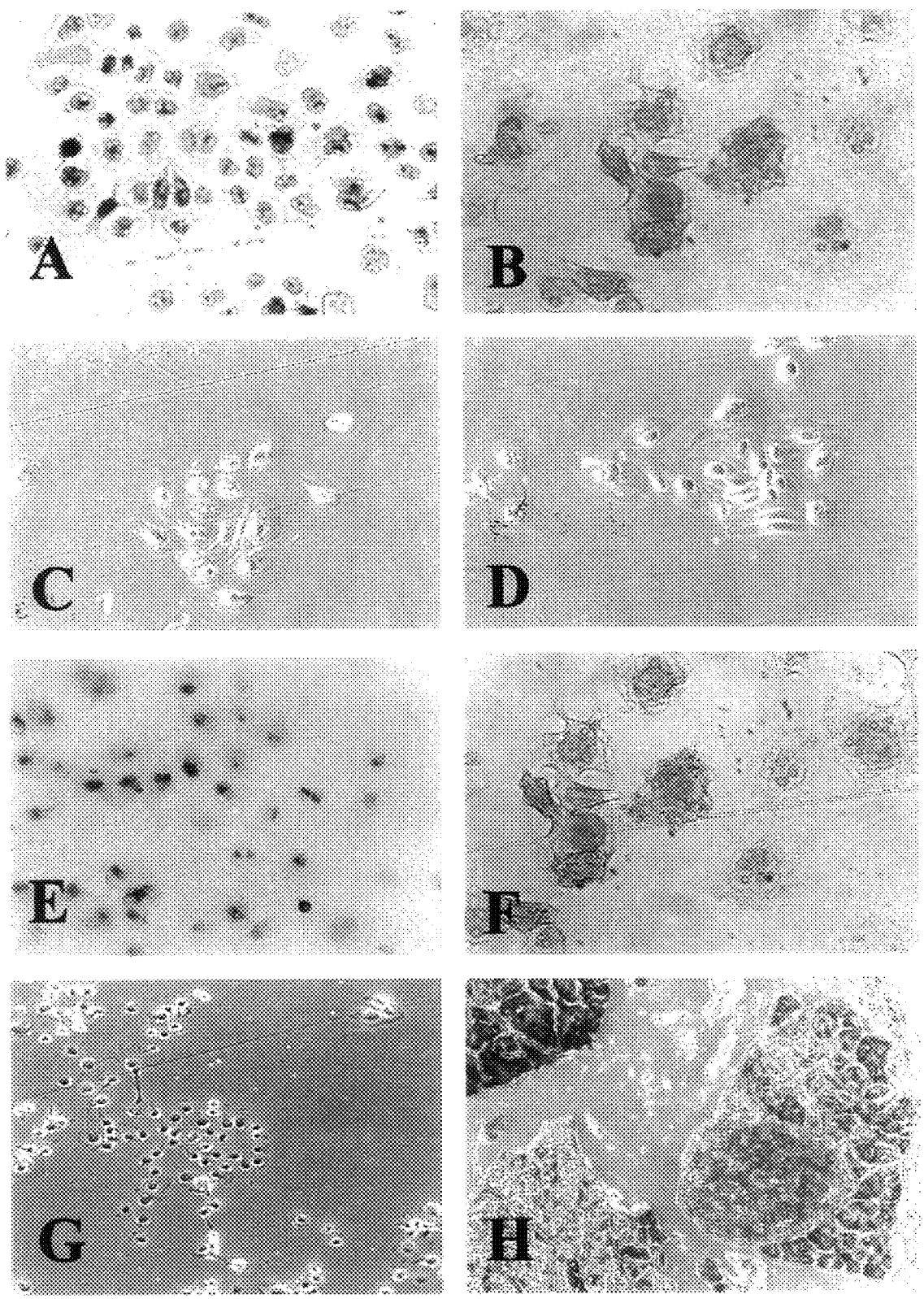
FIGS. 2A–H are photographs showing the immunocytochemistry for insulin of ARIP and PANC-1 cells treated with or without GLP-1. ARIP and PANC-1 cells (transfected with human IDX-1 or solely with a neomycin-resistant gene) were cultured with or without GLP-1 (10 nM) for 72 h and subjected to immunostaining with an anti-human insulin antibody.

FIGS. 2A and 2B show ARIP cells cultured in serum-free medium in the absence (FIG. 2A) or presence (FIG. 2B) of GLP-1. FIGS. 2C and 2D show non-transfected PANC-1 cells cultured in the absence (FIG. 2C) or presence (FIG. 2D) of GLP-1. FIGS. 2E and 2F show PANC-1/IDX-1 cells cultured in the absence (FIG. 2E) or presence (FIG. 2F) of GLP-1. PANC-1/IDX-1 cells, treated with GLP-1 (10 nM for 72 h), and stained solely with secondary antibody, were used as a negative control (FIG. 2G). Rat pancreas was used as a positive control (FIG. 2H). All photographs in FIG. 2 depict their subject magnified 200 times.

FIGS. 3A–I show the immunofluorocytochemistry for IDX-1 of ARIP and PANC-1 cells treated with or without GLP-1. ARIP and PANC-1 cells (transfected with human IDX-1 or solely with a neomycin-resistant gene) were treated with or without GLP-1 (10 nM) for 72 h and subjected to immunostaining with an anti-IDX-1 antibody and with the nuclear dye Hoechst 33242. FIGS. 3A–B show ARIP cells cultured in serum-free medium in the absence (FIG. 3A) or presence (FIG. 3B) of GLP-1. FIGS. 3C and D show non-transfected PANC-1 cells cultured in the absence (FIG. 3C) or presence (FIG. 3D) of GLP-1. FIGS. 3E and F show PANC-1/IDX-1 cells cultured in absence (FIG. 3E) or presence (3F) of GLP-1. FIGS. 3G through 3I show PANC-1/IDX-1 cells stained for insulin alone (FIG. 3G), IDX-1 alone (FIG. 3H) or co-stained for both IDX-1 and insulin (FIG. 3I).

FIGS. 4A and B illustrate the dose- and time-dependent insulin accumulation in the culture medium of ARIP cells. FIG. 4A illustrates dose-dependent insulin secretion into the medium of ARIP cells cultured in serum-free medium containing 12 mM glucose, in the presence or absence of various concentration of GLP-1, for 72 h. The first column (marked "-") represents the insulin level in fresh non-used culture medium; the other columns represent the insulin level in the culture media from ARIP cells cultured in the presence of the indicated concentrations of GLP-1. FIG. 4B illustrates the time course of insulin secretion in medium containing 12 mM glucose, in the presence of GLP-1 (10 nM) for various lengths of time. Values represent the amount of insulin in the medium after the indicated time. Each experiment was repeated at least four times and the data plotted on the graph represent the mean±SD. Statistical significance of the data was evaluated by unpaired Student's t test: *=$p<0.05$; =$p<0.01$; *=$p<0.0001$. (In FIG. 4A, the significance of the data was evaluated by comparing each sample with untreated ARIP cells; in FIG. 4B, the data were evaluated by analyzing the significance of the curve itself by ANOVA).

FIGS. 5A–C illustrate the dose- and time-dependent insulin accumulation in the culture medium of PANC-1 cells. FIG. 5A illustrates the dose-dependent insulin secretion in the medium of PANC-1 cells.cultured in serum-free medium containing 12 mM glucose, in the presence of various concentration of GLP-1. The first column (marked "-") represents the insulin level in fresh non-used culture medium; the other columns represent the insulin level in the culture media from PANC-1 cells cultured in the presence of the indicated concentrations of GLP-1, FIG. 5B represents dose-dependent insulin secretion of PANC-1 cells transfected with human IDX-1 and cultured in serum-free medium containing 12 mM glucose, in the presence of various concentration of GLP-1 for 72 h. The first column (marked"-") represents the insulin level in fresh non-used culture medium; the other columns represent the insulin level in the culture media from cells cultured in the presence of various concentration of GLP-1. FIG. 5C illustrates the time course of insulin secretion into the medium of PANC-1 cells transfected with human IDX-1 and cultured in serum-free medium containing 12 mM glucose, in the presence of GLP-1 (10 nM). Each experiment was repeated at least four times and the data plotted on the graph represent the mean±SD. Statistical significance of the data was evaluated by unpaired Student's t test: *=$p<0.05$; =$p<0.01$; *=$p<0.0001$. No statistical significance was determined for the data presented in FIG. 5A. In FIG. 5B, the significance of the data was evaluated by comparing each sample with untreated PANC-1 cells; in FIG. 5C, the data were evaluated by analyzing the significance of the curve itself by ANOVA.

FIG. 6 illustrates glucose dependent insulin secretion. ARIP (FIG. 6A) and PANC-1 cells (transfected with human IDX-1; FIG. 6B) were cultured in serum-free medium with GLP-1 (10 nM, for 72 h), or vehicle, in the presence of various concentrations of glucose (0, 0.1, 1, 3, 6, 10 and 20 mM). Each experiment was repeated at three times and the data plotted on the graph represent the mean±SD. Insulin levels were normalized for total protein content in each individual sample of culture medium. Statistical significance of the data was evaluated by ANOVA; ***=$p<0.0001$.

Figure 7:
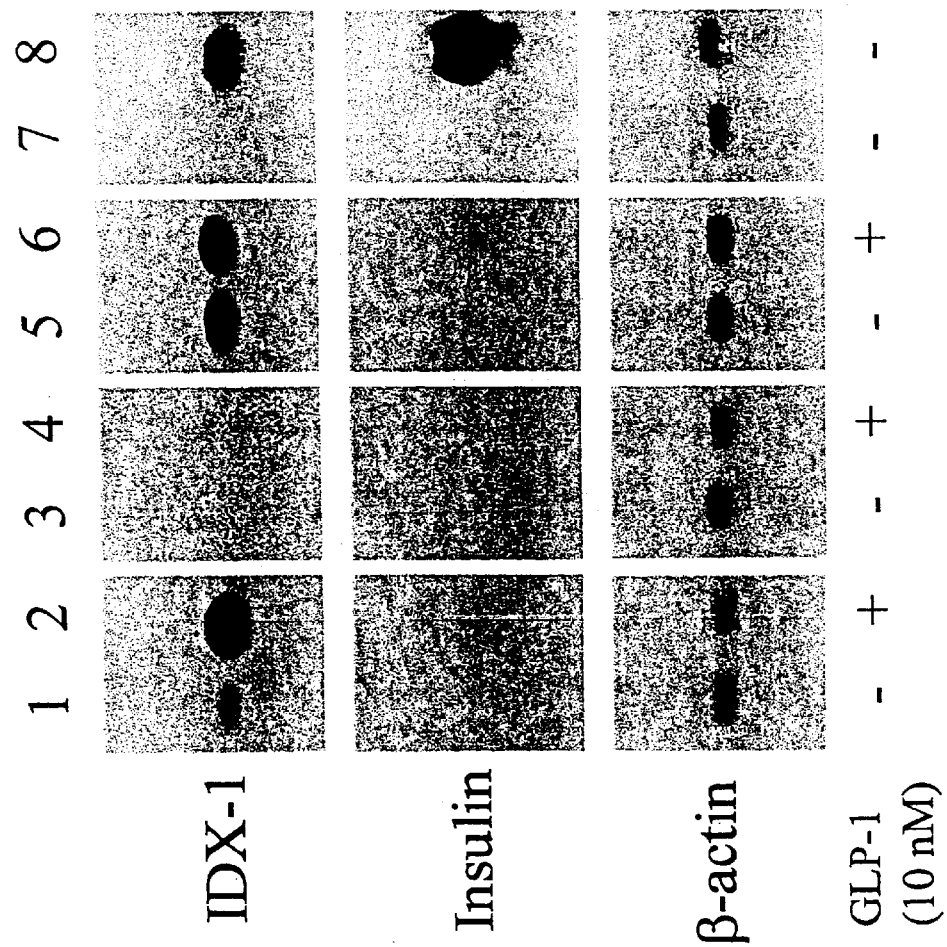

FIG. 7 shows a Northern blot analysis for islet-cell transcripts. ARIP and PANC-1 cells (transfected with human IDX-1, or solely with a neomycin-resistant gene) were cultured in serum-free medium with or without GLP-1 (10 nM, for 72 h) and subjected to northern blot analysis for the detection of IDX-1, insulin, and β-actin mRNAs. Rat pancreas was used as a positive control, rat kidney as a negative control. Lanes 1 and 2: ARIP cells cultured in absence (lane 1), or presence (lane 2) of GLP-1. Lanes 3 and 4: PANC-1 cells cultured in absence (lane 3), or presence (lane 4) of GLP-1. Lanes 5 and 6: PANC-1 cells transfected with human IDX-1 and cultured in absence (lane 5), or presence (lane 6) of GLP-1. Lane 7: rat kidney. Lane 8: rat pancreas. Each experiment was repeated three times, using RNA samples from independent cultures.

FIGS. 8A and 8B show a RT-PCR analysis of islet β-cell specific transcripts. ARIP and PANC-1 cells (transfected with human IDX-1, or solely with a neomycin-resistant gene) were cultured in serum-free medium and treated with GLP-1 (10 nM), vehicle alone, or Exendin-9 (100 nM) and subjected to RT-PCR for insulin, glucokinase (GK), the β-cell glucose transporter GLUT2, and β-actin. FIG. 8A. Lane 1: ARIP cells treated with vehicle alone. Lane 2: ARIP cells cultured in the presence of Exendin-9 (100 nM) for 72 h. Lanes 3 trough 6: ARIP cells treated with GLP-1 for 24 (lane 3), 48 h (lane 4), 72 h (lane 5), and 96 h (lane 6). FIG. 8B. Lanes 1 and 2: PANC-1 cells treated with vehicle alone (lane 1) or GLP-1 (lane 2). Lanes 3 through 7: PANC-1 cells transfected with human IDX-1 and treated with Exendin-9 for 72 h (lane 3) or GLP-1 for 0 (lane 4), 24 (lane 5), 48 (lane 6), 72 (lane 7) and 96 (lane 8) hours. Each experiment was repeated three times, using RNA samples from independent cultures.

FIGS. 9A–C show GLP-1 receptor expression in ARIP and PANC-1 cells. ARIP and PANC-1 cells (transfected with human IDX-1, or solely with the neomycin resistant gene) were cultured in serum-free medium and treated with GLP-1 (10 nM), or vehicle alone, for 72 h. RT-PCR for GLP-R and β-actin was performed with a cycle-titration PCR (15, 20, 25, 30 PCR cycles) to assess the relative abundance of GLP-R transcript. Primers for both transcripts were added together in a single PCR-reaction for each individual sample. FIG. 9A shows ARIP cells cultured with vehicle alone, or GLP-1. FIG. 9B shows PANC-1 cells cultured with vehicle alone, or GLP-I. FIG. 9C shows PANC-1/IDX-1 cells culture with vehicle alone, or GLP-1. Each experiment was repeated four times, using RNA samples from independent cultures. The blots on the left represent one individual experiment, while the graphs on the right are the average of four independent experiments. The numeric values in the graphs represent the ratio of GLP-R mRNA to actin mRNA.

Figure 10:
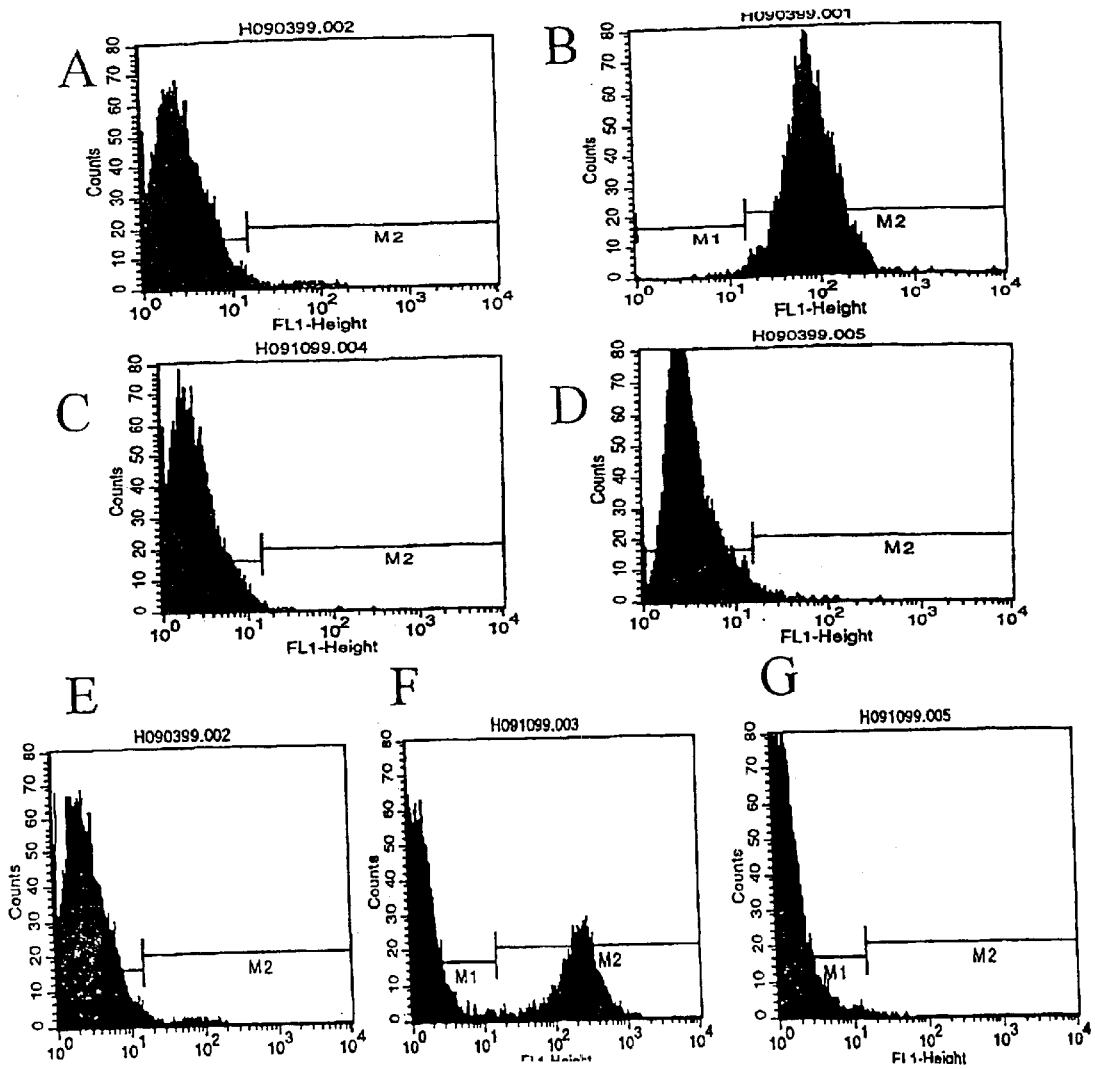

FIG. 10 illustrates a flow cytometric analysis. ARIP and PANC-1 (parental and IDX-1-transfected) cells were treated with GLP-1 (10 Nm) or vehicle for 72 h and stained with fluorescent antibodies against insulin. FIGS. 10A–G show a representative experiment for each individual experimental conditions out of five replicate analyses that were performed. FIGS. 10A and 10B illustrate the results of experiments with ARIP cells cultured in the presence of vehicle (FIG. 10A) or GLP-1 (FIG. 10B). FIGS. 10C and 10D illustrate the results-with parental PANC-1 cells cultured in the presence of vehicle (FIG. 10C) or GLP-1 (FIG. 10D). FIGS. 10E and 10F illustrate the results with PANC-1 cells transfected with human IDX-1 gene cultured in the presence of vehicle (FIG. 10E) or GLP-1 (FIG. 10F). FIG. 10G illustrates the results with PANC-1 cells cultured in the presence of GLP-1 and stained solely with an unspecific isotype-matched FITC-conjugated antibody, without the primary antibody.

FIG. 11 shows the sequence of IDX-1 cDNA [SEQ ID NO: 1] and the protein encoded by it [SEQ ID NO: 2].

DETAILED DESCRIPTION OF THE INVENTION

The present invention is based on the inventor's discovery that the treatment of pancreatic cells with the gastrointestinal incretin hormone glucagon-like peptide-1 (GLP-1) promotes the differentiation of such cells into pancreatic M-like cells; and that, before this can happen, GLP-1 requires the gene expression of the islet differentiation factor IDX-1 to exert its differentiation-promoting activity.

The method of the invention comprises the steps of providing pancreatic cells, transfecting the cells with DNA or mRNA that leads to the expression of IDX-1, and then culturing the cells in human GLP-1.

Any pancreatic cell may be used in the method of the invention, including cells of the islet of Langerhans (such as A, B, D, and F islet cells), epithelial cells of intralobular ducts, acinar cells, centroacinar cells, basket cells, or any other pancreatic exocrine cells—whether they secrete insulin or digestive enzymes—and their associated ducts. In a preferred embodiment of the invention, the cells are obtained from a cell line. As used herein, "cell line" has the usual meaning: a cell culture of a uniform population of cells. Any cell line of pancreatic cells may be used in the method of the invention, including, for example, AsPc-1, AR42J, BxPc-3, Capan-1, Capan-2, Colo357, HPAC, HPAF, HPAF-II, Hs766T, human insulinoma cell line, MiaPaCa, MIAPaCa-2, PANC-1, Panc89, QGP-1, S2CP9, T3M4, or any other pancreatic cell line whether derived from human, rat, or other animal. Use of cells from PANC-1 (human pancreas tumor cell line) is especially preferred.

The cell lines of the invention must express IDX-1 before GLP-1 can cause these cells to differentiate into insulin-secreting cells. If the cells do not already express IDX-1, the method of the invention provides that they are transfected with DNA or mRNA that leads to the expression of IDX-1 is such cells. IDX-1 is well studied; its genetic sequence is known and described. U.S. Pat. No. 6,210,960, for example, the entirety of which is incorporated herein by reference, discusses IDX-1 at length. Any method known in the art of transfecting cells with IDX-1 DNA or its complement may be used in the method of the invention.

In a preferred embodiment, a pancreatic cell line is transfected with a pcDNA3 construct (available from Invitrogen Corp. of Carlsbad, Calif.) that harbors the wild-type full-length IDX-1 cDNA. LIPOTAXI® (available from Stratagene of La Jolla, Calif.) is preferably used as the transfection reagent. The cDNA sequence of IDX-1 is set forth in FIG. 11 as SEQ ID No: 1.

In alternative embodiments, one may use other methods of transfecting cells, such as coprecipitation of DNA with calcium phosphate ($CaPO_4$); "lipofection" with cationic liposomes; transfection with polyethylenimine; transfection by electroporation, in which a single pulse of high-current electricity is applied to a preparation of DNA and cells; receptor-mediated endocytosis; or any other method known to transfer genetic material into cells. The transfection method employed depends on the pancreatic cell used, and should be readily apparent to one of ordinary skill in the art of molecular biology.

After transfecting cells, one then selects cells that are successfully transfected from cells that are not. A preferred method of selecting cells is by transfecting, along with genetic material that encodes IDX-1, genes that confer resistance to drugs which disrupt the cells' growth. A list of gene/drug combinations that may be used to select cells in this manner is set forth below in Table 1:

TABLE 1

Gene/drug combinations that may be used to select cells successfully transfected with genetic material that encodes IDX-1

| RESISTANCE GENE | DRUG |
| --- | --- |
| Aminoglycoside phosphotransferase (AGPT; $neo^r$) | Neomycin geneticin sulfate |
| Hygromycin phosphotransferase ($hyg^r$) | Hygromycin B |
| Puromycin N-acetyl transferase ($puro^r$) | Puromycin |
| Histidinol dehydrogenase (S. typhimurium hisD) | Histidinol |
| Dihydrofolate reductase (DHFR) | Methotrexate |

An especially preferred method of selecting cells is by culturing cells transfected with AGPT in the presence of G418 sulfate (available as "GN-04" from Omega of Tarzana, Calif.). A preferred concentration of G418 sulfate is 400 µg/ml.

Cells successfully transfected with IDX-1 are then cultured in the presence of human GLP-1. Various nutrient mediums are commonly available in which to culture cells; any medium which provides nutrients to promote cell growth may be used. When using PANC-1 cells, a preferred medium is DMEM medium supplemented with 10% fetal calf serum (available from Gibco-BRL of Gaithersbrug, Md.), 100 µg/ml penicillin, and 50 µg/ml streptomycin. The cells may be grown under any room conditions suitable for the propagation of cells; in a preferred embodiment, cells are grown at 37° C. under a humidified condition of 95% air and 5% $CO_2$.

GLP-1 may be added to culture at any time, but is preferably added after cells have an opportunity to propagate. In a preferred embodiment, GLP-1 is added after cells have grown to 80% of confluence. GLP-1 may be added at any concentration between 0.1 nM and 1 M. A concentration of 1–20 nM is preferred for PANC-1 cells, and a concentration of 10 nM is especially preferred. Cells may be cultured in the presence of GLP-1 for anywhere between 1 hour and 10 days, but a culture time of 24–72 hours is preferred, and a culture time of 48 hours is especially preferred.

GLP-1-treated cells contain and secrete the counterpart protein, as demonstrated by immunocytochemistry, RIA, and PACS analysis. GLUT2 is the first β-cell specific transcript one detects in GLP-1-treated pancreatic ductal cells. This is followed by insulin and finally by the glucose-phosphorylating enzyme, glucokinase. The specificity of the effect of GLP-1 is validated by experiments demonstrating that treatment of cells (ARIP or PANC-1) with the GLP-1 receptor antagonist Exendin-9 inhibits the expression of β-cell-specific genes.

The cell lines of the invention may be used to investigate the development and function of the pancreas, the cells that constitute it, and the secretions it makes. They may also be used to investigate the efficacy of drugs that promote insulin secretion. As previously discussed, such drugs are commonly administered to patients with type II diabetes, who often display a resistance to insulin. These drugs include sulfonylureas, repaglinide, metformin, troglitazone, and others. One could test these drugs according to the usual protocol: obtain a cell line according to the invention; expose the drug to be tested to the cell line; measure the insulin secreted. The cell line of the invention better approximates the behavior of human insulin-secreting cells better than any cell line of the prior art. This is principally because 1) the cell line may be derived from human cells, such as PANC-1; and 2) the cell line secretes insulin in a glucose-dependent manner.

EXAMPLES

The Examples discussed herein demonstrate that only those pancreatic epithelial cells that express IDX-1 are susceptible to undergo differentiation into insulin secreting cells once they are treated with GLP-1. Interestingly, the overexpression of human IDX-1, by means of stable cellular transfection, is not sufficient, per se, to induce the differentiation of these cells into a β-cell-like phenotype. It is only when IDX-1-positive cells are exposed to GLP-1 that they acquire the ability of synthesizing insulin. Similarly, it is not the presence of receptors for GLP-1, per se, that allows for the differentiation of GLP-1 treated cells into insulin secreting cells. Indeed, while only parental ARIP cells are able to differentiate into insulin secreting cells after treatment with GLP-1, both ARIP and PANC-1 cells constitutevely express receptors for GLP-1. PANC-1 cells respond to GLP-1 by means of differentiation into insulin secreting cells only when transfected with human IDX-1. Treatment with GLP-1 increases IDX-1 mRNA levels and transfection with IDX-1 induces an increase in GLP-1 receptor mRNA levels, suggesting a further interplay between IDX-1 and GLP-1. The following observations clearly indicate that GLP-1 is able to induce a β-cell-like phenotype only in cells that are genetically susceptible to acquire that phenotype, and IDX-1 is a key player in this process.

Preparation of Cell Culture

Rat (ARIP) and human (PANC-1) ductal cell lines were respectively a gift from Dr. J. M. Egan (National Institute on Aging, Baltimore, Md.) or purchased from ATCC (American Type Culture Collection; Manassas, Va.). ARIP cells were cultured in F12 medium (Gibco-BRL, Gaithersburg; Md.) containing 100 μg/ml penicillin, 50 μg/ml streptomycin and 10% fetal calf serum (FCS; Gibco-BRL) at 37° C. under a humidified condition of 95% air and 5% $CO_2$. PANC-1 cells were cultured in DMEM medium supplemented with antibiotics and FCS, as indicated for F12 medium. Treatment with human GLP-1 (H-6795, Bachem; King of Prussia, Pa.) was carried out using cells grown to 80% of confluence, after washing the cell layer with serum-free medium and a "wash-out" incubation for 6-h with serum free medium. To determine dose response to GLP-1, cells were cultured with fresh serum-free medium containing increasing concentration of GLP-1 (0.1, 1, 10, 20 nM), or vehicle alone. At the completion of the experiment, media and cells were collected. To determine the time course of response, cells were cultured in serum-free medium with GLP-1 (10 nM) for 0, 12, 24, 48, 72 or 96 h. Control dishes were cultured with vehicle alone, or with the peptide receptor antagonist of GLP-1, Exendin-9 (100 nM) for 72 h (gift Dr. J. M. Egan). The glucose concentration in the culture medium was 12 mM for both cell lines.

Cell Transfection With Human IDX-1 cDNA

PANC-1 cells were transfected with a pcDNA3 construct (Invitrogen; Carlsbad, Calif.) harboring the wild-type full-length IDX-1 cDNA using LipoTAXI (Catalog N. 204110; Mammalian Transfection Kit, Stratagene; La Jolla, Calif.). Control cells were transfected with the vector alone. The selection of positive (i.e. transfected) cells was carried out by culturing the cells in the presence of 400 μg/ml of G418 sulfate (GN-04, Omega; Tarzana, Calif.).

Immunocytochemistry and Immunofluorescence Microscopy

Cells were cultured on monocoated chamber slides (Nalge Nunc International; Naperville, Ill.) in the presence of GLP-1 (10 nM), or vehicle, for 72 h.

For the detection of insulin, cells were washed and fixed with 3% paraformaldehyde for 4 h, at room temperature in PBS, solubilized with 0.1% (vol/vol) Triton X-100 in PBS for 5 min. Cells were then incubated sequentially with an anti-insulin antibody and a secondary antibody, as described by the manufacturer (Biomeda Corp.; Foster City, Calif.). The cells were examined using a Ziess Axiophoto microscope (New York, N.Y.).

For the detection of IDX-1, slightly different conditions were used. Briefly: the concentration of paraformaldehyde was decreased to 2%, and the concentration of Triton to permeabilize the cells was raised to 0.2% Triton-X-100. Cells were then washed with 0.01 M PBS three times for 3–5 min, and non-specific binding was inhibited by using 5% chick serum in 0.01 M PBS, at room temperature for 60 min in a humid chamber. A rabbit IDX-1 antibody directed against the N-terminus of the frog homologue of the IDX-1 gene was used as the primary antibody (1:500 diluted with 0.1% Triton-X 100, 1% BSA in 0.01 M PBS), and slides were incubated at 4° C. overnight in a humid chamber. After washing, cells were incubated with a fluorescein-conjugated goat anti-rabbit IgG antibody (Molecular Probes, Inc. Eugene, Oreg.) and incubated at room temperature for 1 hour in a humid chamber. Nuclei of cells stained with anti-IDX-1 antibody were visualized with Hoechst 33242 dye (Sigma, St. Louis, Mo.). The percentage of IDX-1 containing cells was evaluated by counting the number of IDX-1 "positive" cells divided by the total number of cells identified by nuclear staining.

Insulin immunofluoresce, for co-immunostaining with IDX-1, was carried on using the same primary antibody described in the previous paragraph, while the secondary antibody was a goat anti-guinea pig IgG (Molecular Probes, Inc.). The cells were examined using a using a fluorescent microscope (E-800; Nikon, Tokyo).

Staining for insulin and IDX-1 experiments was repeated at least three times, using independent cell cultures.

Hematoxylin and eosin staining was employed, in some experiments, to show the morphological changes observed under the experimental conditions described below.

Measurement of Insulin Secretion

PANC-1 (parental, IDX-1-transfected, and neomycin-transfected) cells and ARIP (only parental) cells were plated at density of $10^6$ cells/well in a 6 well plate. Once the cells reached 80% of confluence, they were washed with serum-free medium containing 12 mM glucose and exposed to fresh serum-free medium for increasing length of time (0, 12, 24, 48, 72, 96 h) in the presence of various concentrations of GLP-1 (0.1, 1, 10, 20 nM) or vehicle. Glucose-dependent insulin secretion was evaluated by culturing the cells in the presence of a determined concentration of GLP-1 (10 nM for 72 h) with increasing concentration of glucose in the culture medium (0, 0.1, 1, 3, 6, 10 and 20 nM). Insulin released into the medium was measured by RIA (Linco Research Inc.; St. Charles, Mass.). Total insulin accumulation in the culture medium was then normalized for total cellular protein content per each Individual cultures.

Protein Assay

Total cellular protein content was measured by utilizing the Bradford method (Bio-Rad; Richmond, Calif.). The amount of proteins measured was used as a correction factor for determining the relative amount of medium to be assayed for each individual RIA for insulin.

RNA Isolation and Northern Blot Analysis

Cellular RNA was extracted as routinely described. Northern blots were hybridized with: 1) full length rat insulin II cDNA probe; 2) human IDX-1 cDNA; 3) rat β-actin cDNA probe. All cDNA probes were labeled with [$^{32}$P]dCTP (Amersham Life Science; Arlinghton Heights, Ill.) by the random priming procedure using the enzyme sequenace (United States Biochemical; Cleveland, Ohio). Hybridization and washing conditions were carried out as previously described. Y. Wang et al., Glucagon-like peptide-1 can reverse the age-related decline in glucose tolerance in rats," *J. Clin. Invest.* 99:2883–2889 (1997). Messenger RNA levels for individual transcripts were evaluated by densitometric analysis and normalized for the relative abundance of β-actin mRNA.

RT-PCR and Southern Blot Analysis

After the treatment of ARIP and PANC-1 cells with GLP-1, Exendin-9, or vehicle, for the described length of time and the various doses, the culture medium was removed and the cells were washed (twice) with serum-free medium. Total RNA was isolated using the TRiazol-method (Gibco-BRL), and treated with DNase (Amplification Grade, GibcoBRL) in 20 mmol/l Tris-HCL (pH 8.4), 2 mmol/l $MgCl_2$, and 50 mmol/l KCl to remove any traces of contaminating genomic DNA. RNA (2.5 µg) was then subjected to reverse transcription (RT reagents; Promega; Madison, Wis.). RT-PCR was undertaken in a volume of 50 µl of buffer containing 50 mmol/l KCl, 10 mmol/l Tris-HCl, 3.5 mmol/l $MgCl_2$, 200 µmol/l each dNTPs, and 0.4 µmol/l each of sense and antisense primers to rat or human insulin (depending on the specific cell from which the RNA was extracted). Amplification was performed for 30 cycles at the denaturing temperature of 94° C. for 1 min, annealing temperature of 60° C. for 45 sec, and an extension temperature of 72° C. for 1 min. For the amplification of GLUT2 and individual cells revealed some additional, although less evident, changes. These included more irregular and variable cell shapes, with a cytoplasm less homogenous and "rougher" in appearance than control culture.

Morphological Changes of PANC-1 Cells Induced by GLP-1

Figure 1:
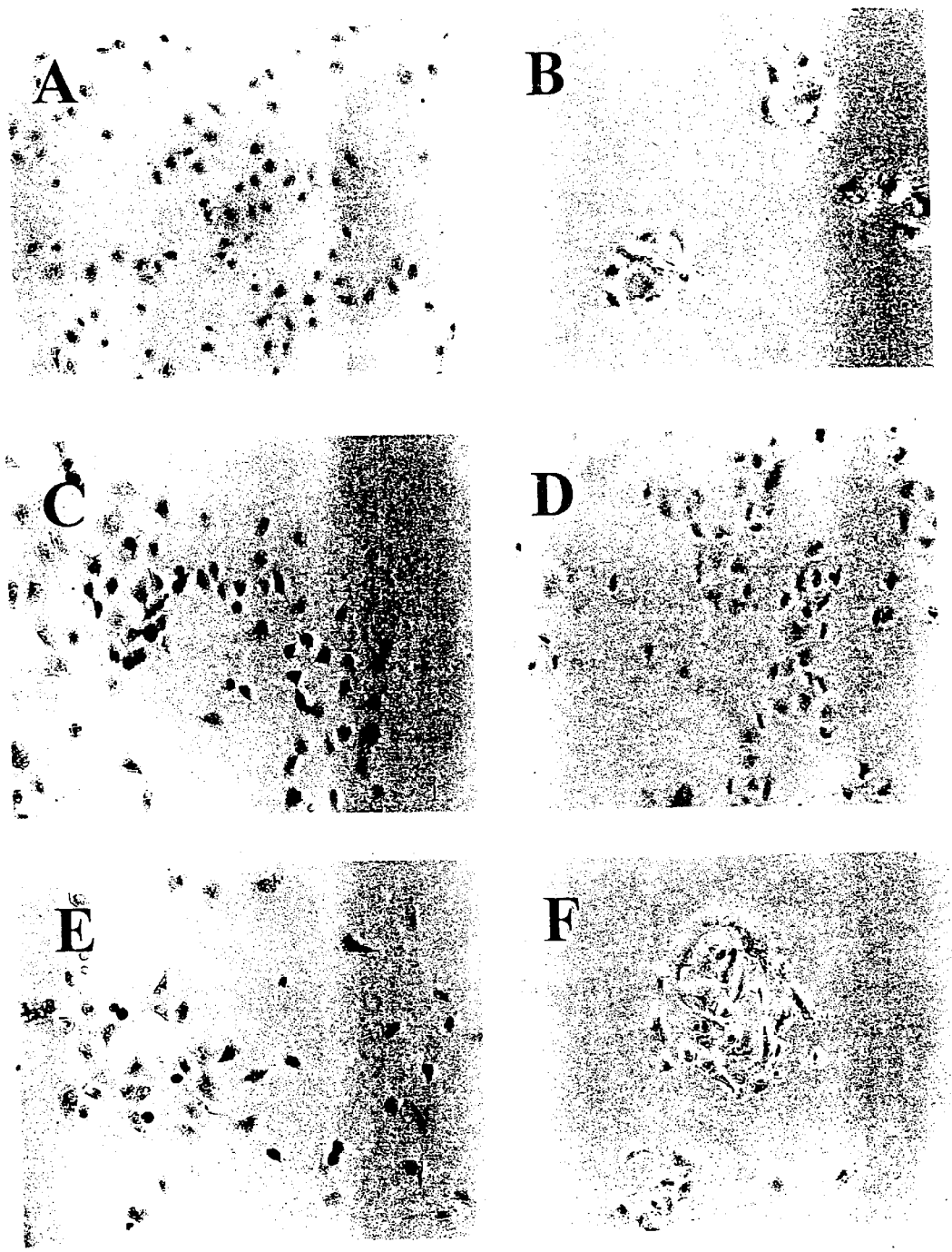
FIGS. 1A–F are photographs showing the morphological changes of rat pancreatic tumor duct cells (ARIP) and human pancreatic tumor duct cells (PANC-1) cells treated with GLP-1. ARIP and PANC-1 cells (transfected with human IDX-1 or solely with a neomycin-resistant gene) were cultured in serum-free medium with or without GLP-1 (10 nM) for 72 h, and stained with hematoxylin and eosin.

Parental (non-transfected) PANC-1 cells did not respond to GLP-1 (10 nM, for 72 h) with any morphological change (FIG. 1, Panel C for vehicle alone; Panel D for GLP-1-treatment). Transfection with human IDX-1 induced clear changes in the shape of individual cells, as well as, in the relationship between cells (FIG. 1, Panel D). IDX-1-transfected cells grew in patches rather than isolated and were surrounded by a large amount of extracellular matrix (FIG. 1, Panel E). Treatment of IDX-1-transfected PANC-1 cells with GLP-1 (10 nM, for 72 h) further promoted the tendency of forming few-cells aggregates (FIG. 1, Panel F). In addition, GLP-1 induced an increase in the size of individual cells (FIG. 1, Panels E and F).

Immunocytochemistry for Insulin

Treatment with GLP-1 induces the differentiation of ductal epithelial cells into insulin-producing cells. FIG. 2 illustrates a series of cell cultures grown with or without GLP-1 (10 nM) for 72 h. Using anti-insulin antibody, a positive immunoreactivity for insulin was detected in GLP-1-treated ARIP cells (FIG. 2, Panel B); in contrast, no insulin immunoreactivity was observed in ARIP cells cultured with vehicle alone (FIG. 2, Panel A). Preabsorption of the antibody with an excess of human recombinant insulin prevented the staining of insulin-positive GLP-1 treated cells (data not shown). While treatment with GLP-1 turned the majority of ARIP cells into glucokinase mRNAs, the same PCR conditions as described above were used in the presence of gene-specific primers. For β-actin, the annealing temperature was raised to 64° C. for 1 min and gene-specific primers were used. For GLP-1-receptor (GLP-R) the annealing temperature used was 55° C. All other experimental conditions to amplify GLUT2, glucokinase, and GLP-R mRNAs were identical to those described for the amplification of insulin mRNA. Primer sequences for human and rat insulin, GLUT2, glucokinase, GLP-R, and β-actin are presented in Table 2. RT and PCR conditions for human transcripts were identical to those described for rat mRNAs.

TABLE 2

PCR information

| TARGET GENE | PRIMER SEQUENCE | SIZE OF PCR PRODUCT (BP) |
| --- | --- | --- |
| RAT | | |
| Insulin | CCTGCCCAGGCTTTTGTCAA(+)<br>CTCCAGTGCCAAGTCTGAA(−) | 187 |
| GLUT2 | TTAGCAACTGGGTCTGCAAT(+)<br>GGTGTAGTCCTACACTCATG(−) | 343 |
| GK | AAGGGAACAACATCGTAGGA(+)<br>CATTGGCGGTCTTCATAGTA(−) | 136 |
| β-Actin | CGTAAAGACCTCTATGCCAA(+)<br>AGCCATGCCAAATGTCTCAT(−) | 349 |
| GLP-R | TCTCTTCTGCAACCGAACCT(+)<br>CTGGTGCAGTGCAAGTGTCT(−) | 350 |
| HUMAN | | |
| Insulin | CTCACACCTGGTGGAAGCTC(+)<br>AGAGGGAGCAGATGCTGGTA(−) | 212 |
| GLUT2 | AGCTTTGCAGTTGGTGGAAT(+)<br>AATAAGAATGCCCGTGACGA(−) | 300 |
| GK | TGGACCAAGGGCTTCAAGGCC(+)<br>CATGTAGCAGGCATTGCAGCC(−) | 207 |
| β-Actin | GTGGGGCGCCCCAGGCACCA(+)<br>CTCCTTAATGTCACGCACGATTTC(−) | 392 |
| GLP-R | GTGTGGCGGCCAATTACTAC(+)<br>CTTGGCAAGTCTGCATTTGA(−) | 347 |

Southern blotting with species-specific full length cDNA probes for insulin, GLUT-2, glucokinase, GLP-1 receptor and β-actin was performed as previously described. Y.

Wang, R. Perfetti, N. H. Greig, H. W. Holloway, K. A. DeOre, C. Montrose-Rafizadeh, D. Elahi, J. M. Egan, "Glucagon-like peptide-1 can reverse the age-related decline in glucose tolerance in rats." *J Clin Invest* 99:2883–2889, 1997.

Flow Cytometric Analysis

For fluorescence-activated cells sorting (FACS) analysis, cells were cultured in the presence of GLP-1 (10 nM), or vehicle, for 72 h, then washed with cold PBS (pH 7.4; three times) and incubated overnight, on ice, in PBS with 2% paraformaldehyde. After centrifugation, the cell pellet was resuspended in 400 $\mu$l of cold 0.1% Triton diluted in FACS buffer (PBS with 2% FCS). After several centrifugation and washes, the cells were resuspended in the assay buffer with of 10 $\mu$l of fluorescent-conjugated insulin antibody (Cat N. FM205, FITC: Chromaprobe, Inc; Mountain View, Calif.), in the presence of 10 $\mu$l of blocking antibody (anti-mouse IgG; Organon Teknika-Cappel, West Chester, Pa.). Control samples were treated with PBS, without the primary antibody, and then incubated with an isotope-matched FITC-conjugated control antibody (murine IgG; Chromaprobe Inc., Mountain View, Calif.). Flow cytometric analysis was performed with a FACScan[R] cytometer, using the LYSYS II program, and by fluorescence microscopy, as is well known in the art. See, e.g., E. Elstner, M. Linker-Israeli, J. Le, T. Umiel, P. Michl, J. W. Said, L. Binderup, J. C. Reed, H. P. Koeffler, "Synergistic decrease of clonal proliferation, induction of differentiation, and apoptosis of acute promyelocytic leukemia cells after combined treatment with novel 20-epi vitamin D3 analogs and 9-cis retinoid acid." *J Clin Invest* 99:349–360, 1997.

Cell viability was evaluated by the Trypan blue dye (Gibco-BRL) exclusion technique.

Statistical Analysis

The data were expressed as mean±S.E. Significance of the data was evaluated by unpaired Student's t test. One-way analysis of variance (ANOVA) was used to evaluate statistical significance when more than two data points were analyzed. Statistical analyses by unpaired Student's t test or ANOVA are explicitly identified in the text or in the figure legends.

EXPERIMENTAL RESULTS

Morphological Changes of ARIP Cells Induced by GLP-1

Various changes in the morphology of ARIP cells resulted from the treatment with GLP-1 (10 nM) for 72 h. GLP-1 primarily affected the relationship between cells within a given culture dish, with an additional, although much less evident, effect on the appearance of individual cells. While naive ARIP cells characteristically grew as individual cells forming a fine monolayer (FIG. 1, Panel A), treatment with GLP-1 promoted the aggregation of cells in small clusters (FIG. 1, Panel B). This was not a function of cell density: treatment with GLP-1 induced ARIP cells to aggregate in patches even when plated at a very low density. Although the majority of GLP-treated cells tended to grow in semi-spherical patches of cells, a small percentage of cells continued to grow as sparse and isolated cells, indicating that there was heterogeneity of response to GLP-1. The morphology of insulin-producing cells, a minority of cells never acquired these features in response to GLP-1, and never gained the ability to synthesize insulin.

No positive insulin immunostaining was observed with parental PANC-1 cells cultured in the presence or absence of GLP-1 (FIG. 2, Panels D and C). Transfection of human PANC-1 cells with human IDX-1 was able to render these cells capable of synthesizing insulin when exposed to GLP-1 (FIG. 2, Panel F). In contrast PANC-1 cells cultured with vehicle alone were insulin negative, even when transfected with human IDX-1 (FIG. 2, Panel E). A negative control was obtained by using the solely the secondary antibody to stain a culture of PANC-1-IDX-transfected cells cultured in the presence of GLP-1 (10 nM) for 72 h (FIG. 2, Panel G). A section of rat pancreas was used as a positive control for insulin immunostaining (FIG. 2, Panel H).

Immunofuorochistochemistry for IDX-1

ARIP and PANC-1 (parental and IDX-1-transfected) cells were cultured as described for insulin immunostaining and subjected to immunofluorescence study for IDX-1. Control nuclear staining was performed for all culture conditions. Using anti-IDX-1 antibody, a positive immunoreactivity for IDX-1 was detected in ARIP cells treated with vehicle alone (FIG. 3, Picture A) or GLP-1 (FIG. 3, Picture B). No positive IDX-1 staining was observed with parental PANC-1 cells cultured with vehicle alone or GLP-1 (FIG. 3, Pictures C and D). Transfection of human PANC-1 cells with human IDX-1 induced, as expected, the expression of the counterpart protein (FIG. 3, Pictures E and F). Treatment with GLP-1 (10 nM for 72 h) promoted a further increase the expression level of IDX-1, for both ARIP and PANC-1/IDX-1-transfected cultures (FIG. 3, Pictures B and F). It appeared that GLP-1 increased the level of expression of IDX-1 rather than number of IDX-1 expressing cells. Counting of 400 cells from several independent cultures of.ARIP and PANC/IDX-1 cells treated with GLP-1 or vehicle revealed that approximately 70% of ARIP and 100% of PANC/IDX-1 cells expressed IDX-1.

Double immunofluorescence for insulin and IDX-1 of PANC-1/IDX-transfected cells cultured with GLP-1 (10 nM, 72 h) demonstrated that the two proteins were co-expressed under the experimental conditions described (FIG. 3, Picture G, staining for insulin; Picture H, staining for IDX-1; Picture I, double immunostaining for insulin and IDX-1). Approximately 85% of IDX-1 containing cells were also positive for the presence of intracellular insulin. All insulin-containing cells were positive for IDX-1 staining; the anti-insulin antibody did not stain few weekly IDX-1 positive cells (~20% of PANC-1/IDX-1 cells).

Insulin Release in the Culture Medium

Figure 4:
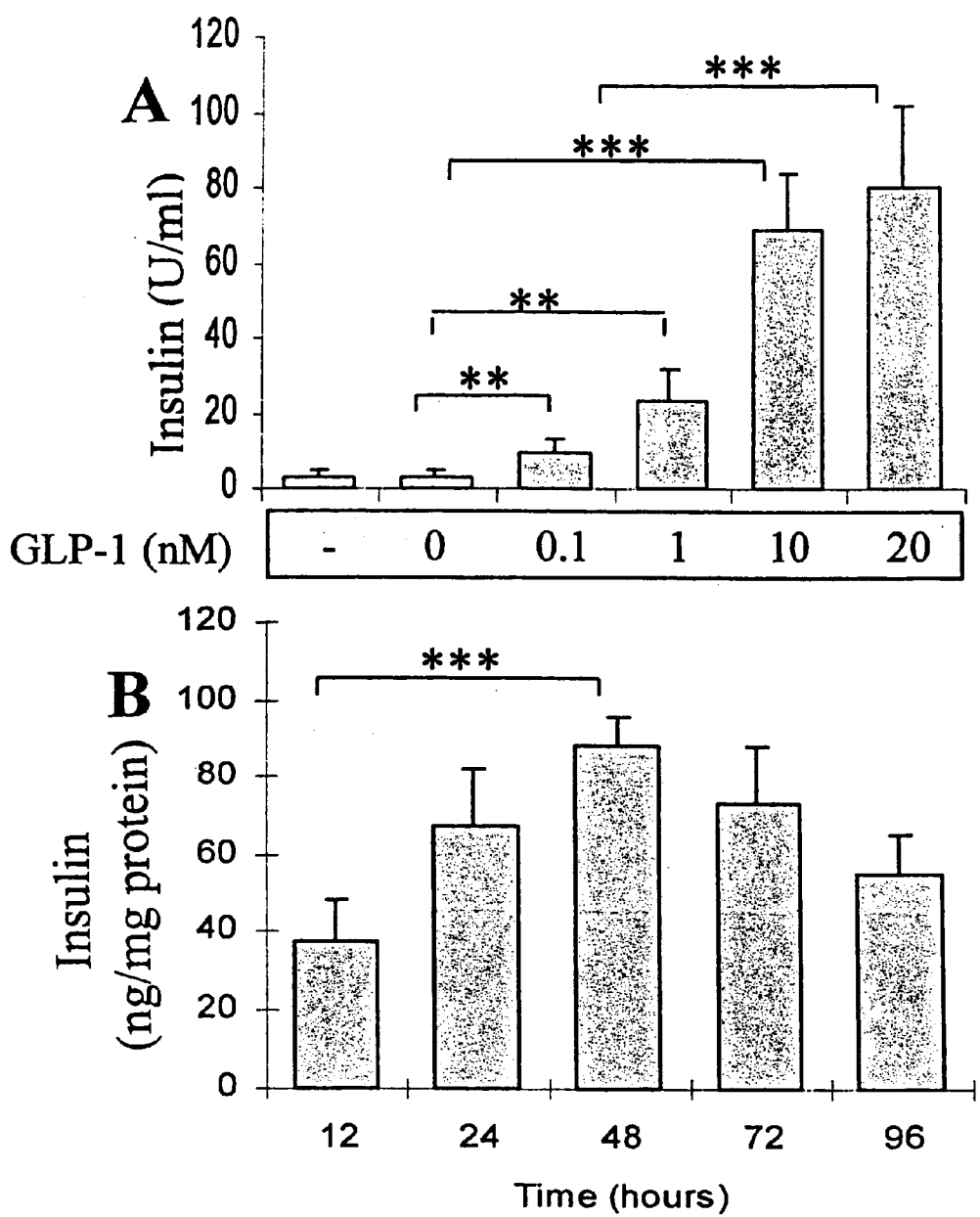

ARIP cells cultured in the presence of GLP-1 exhibited a dose-dependent response of insulin secretion (FIG. 4, Panel A). The minimum concentration of GLP-1 required to "transform" rat pancreatic (ARIP) ductal cells into insulin producing cells was 1 nM. A linear increase of insulin accumulation into the culture medium was observed with increasing doses, and a plateau of this response was detected with 20 nM of GLP-1. Analysis of the time course of the insulin secretory response of ARIP cells cultured in the presence of GLP-1 (10 nM) revealed that the maximal secretion was observed at 48 h, with a plateau at 72 h, followed by an early decline at later time points (FIG. 4, Panel B).

Figure 5:
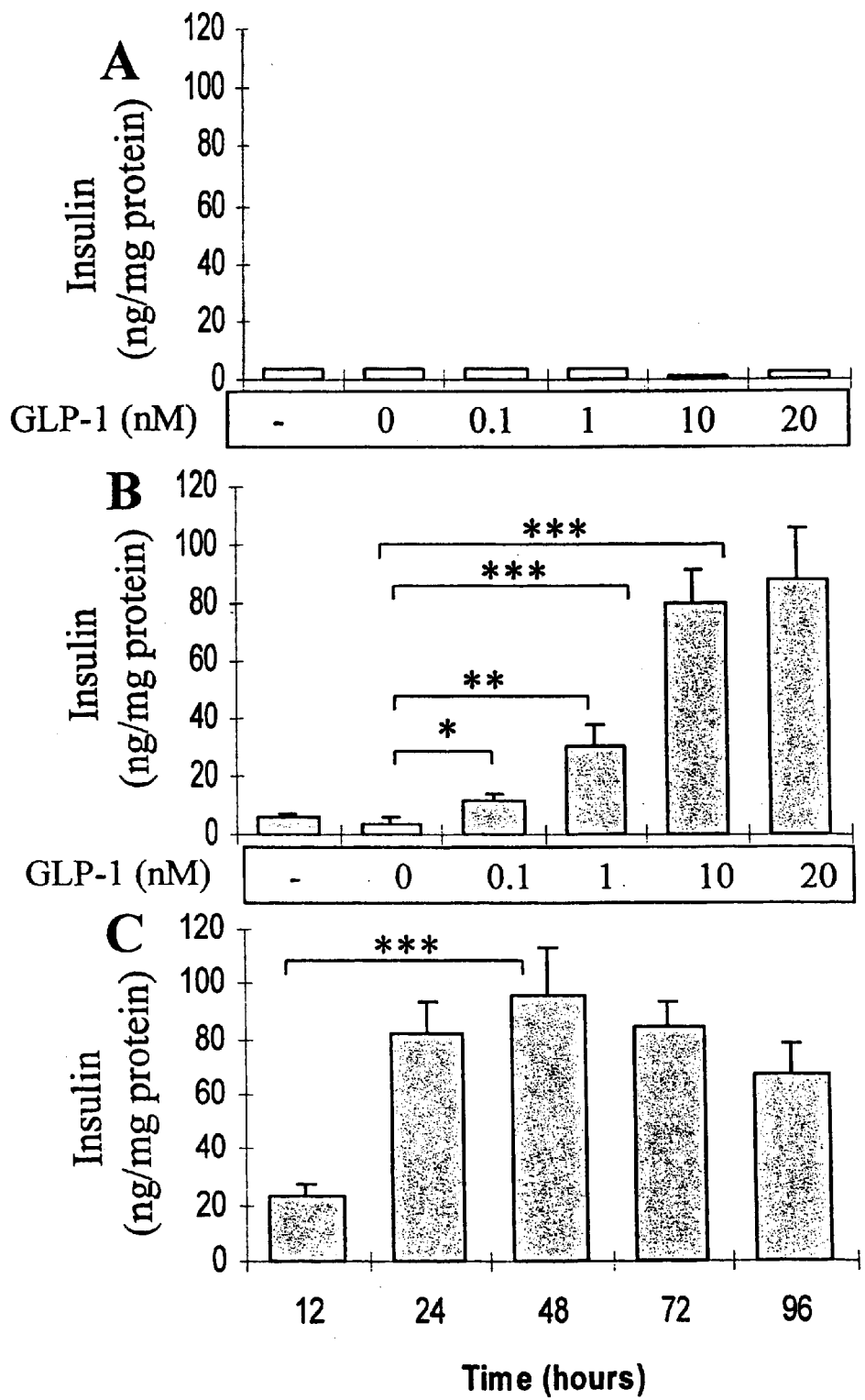

The results described above for ARIP cells treated with GLP-1 were not confirmed when a different ductal cell line (human PANC-1) was used to perform a similar set of experiments. PANC-1 cells did not secrete insulin in response to GLP-1 (FIG. 5, Panel A). However, cellular transfection of PANC-1 cells with the human β-cell differentiation factor IDX-1 rendered the human ductal cells capable of responding to GLP-1 and induced the synthesis and secretion of insulin. A concentration of GLP-1 in the culture medium of 1 nM was required to induce insulin secretion and to promote a dose-dependent accumulation of insulin in the culture medium (FIG. 5, Panel B). The time course of the GLP-1 response revealed a peak secretion within 48 h, with a plateau at 72 h and an early decline after 96 h from the first exposure to GLP-1 (FIG. 5, Panel C).

Cell culturing in the presence of increasing concentration of glucose with a constant concentration of GLP-1 (10 nM for 72 h), or vehicle, revealed that both ARIP and PANC-1/IDX-1 transfected cells, were able to release insulin in a glucose-dependent manner when exposed to GLP-1 (FIG. 6, Panels A and B). No insulin secretory response was observed with wild-type PANC-1 cells cultured in the presence of GLP-1 (10 nM, for 72 h) with increasing concentration of glucose in the culture medium (data not shown). For both ARIP and PANC-1/IDX-1 cells the lowest concentration of glucose required to induce the secretion of insulin was 3 mM. A linear increase of insulin accumulation into the culture medium was observed with increasing doses ($p<0.001$), and a plateau of this response was detected with glucose concentrations between 10 and 20 mM (FIG. 6, Panels A and B).

Messenger RNA Levels of β-Cell Specific Genes

Rat (ARIP) and human (PANC-1) ductal epithelial cells were subjected to northern blot analysis for detection of IDX-1, insulin, and β-actin mRNA levels. While ARIP cells showed that the IDX-1 gene was constitutively transcribed, PANC-1 cells were IDX-1-negative (FIG. 7). Hybridization of the same blot with insulin cDNA probe was negative both for ARIP and PANC-1 cells (FIG. 7).

To analyze the ability of GLP-1 to induce the differentiation of ductal cells into insulin-producing cells, RT-PCR analysis was begun to achieve maximum sensitivity for the detection of insulin mRNA, as well as the mRNA for other β-cell-specific transcripts. RT-PCR analysis was performed using RNA isolated from at least five different cultures for each experimental condition, and each PCR reaction was repeated more than two times.

Figure 8:
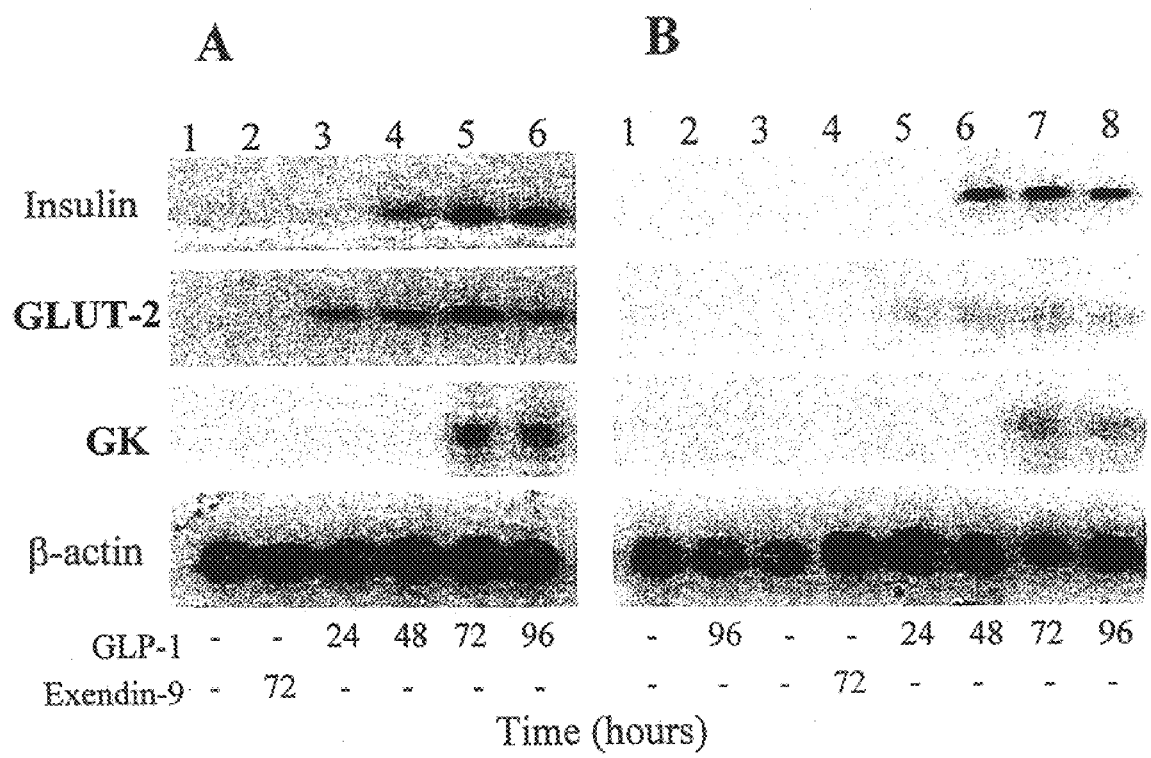

RT-PCR analysis of ARIP cells demonstrated that the lowest concentration of GLP-1 required for the initial detection of insulin mRNA was that of 1 nM (data not shown). To evaluate the time course of response to GLP-1, ARIP cells were cultured in serum-free medium with GLP-1 (10 nM) for an increasing length of time (FIG. 8, Panel A). A clear band at 187 bp corresponding to rat insulin I and II mRNA was detected first in ARIP cells cultured with GLP-1 for 48 h. This was followed by a plateau at 72 h, with insulin mRNA levels remaining constant up to 96 h after the first GLP-1 exposure. No RT-PCR products were detected in the negative control or in non-GLP-1-treated cells. RT-PCR for GLUT2 revealed the presence of this transcript (343 bp) after only 24 h of treatment with GLP-1, preceding the earliest detection of insulin mRNA by approximately one day. After the initial expression at 24 h, GLUT2 mRNA remained constant over time, in a fashion similar to insulin. Glucokinase mRNA was detectable at 72 h, 24 h after the appearance of insulin mRNA, indicating that the glucose-sensing ability of insulin-secreting cells was a late event in the differentiation process. Glucokinase mRNA levels remained unchanged after the 72 h detection. No RT-PCR products were detected in the negative control or in non-GLP-1 treated cells. This leaves the sequence of gene expression as GLUT2 at 24 h, insulin at 48 h, and glucokinase at 72 h. RT-PCR for β-actin was used as a control for RNA loading.

RT-PCR for insulin using RNA extracts obtained from PANC-1 cells treated for 96 h with GLP-1 (10 nM) were consistently negative (FIG. 8, Panel B). Transfection of PANC-1 cells with human IDX-1 was not able, per se, to induce insulin gene transcription, however it was sufficient to render PANC-1 cells responsive to GLP-1. The lowest dose of GLP-1 required to detect insulin mRNA was 1 nM (data not shown). This was followed by a progressive dose dependent increase of insulin mRNA levels, reaching a peak at 10 nM and a plateau at 20 nM (data not shown). The time course of response in PANC-1 cells transfected with human IDX-1 and cultured with GLP-1 (10 nM) revealed the earliest detection of insulin after 48 h, followed by a plateau at 72 h. RT-PCR for β-actin was used as a control for RNA loading. The pattern of expression for GLUT2 and glucokinase mRNAs was similar to the one described for ARIP cells treated with GLP-1, with GLUT2 preceding the earliest insulin gene expression by 24 h, and glucokinase-appearing only 24 h after the first detection of insulin mRNA. This leaves the sequence β-cell specific genes in PANC-1 as GLUT2 at 24 h, insulin at 48 h, and glucokinase at 72 h.

Treatment of either ARIP or PANC-1/IDX-1 cells with the GLP-1 receptor antagonist, Exendin-9, inhibited the expression of GLUT-2, insulin and glucokinase (FIG. 8, Panels A and B), demonstrating that the β-cell-like phenotype observed, under the experimental conditions described in the present study, was specifically induced by GLP-1.

Figure 9:
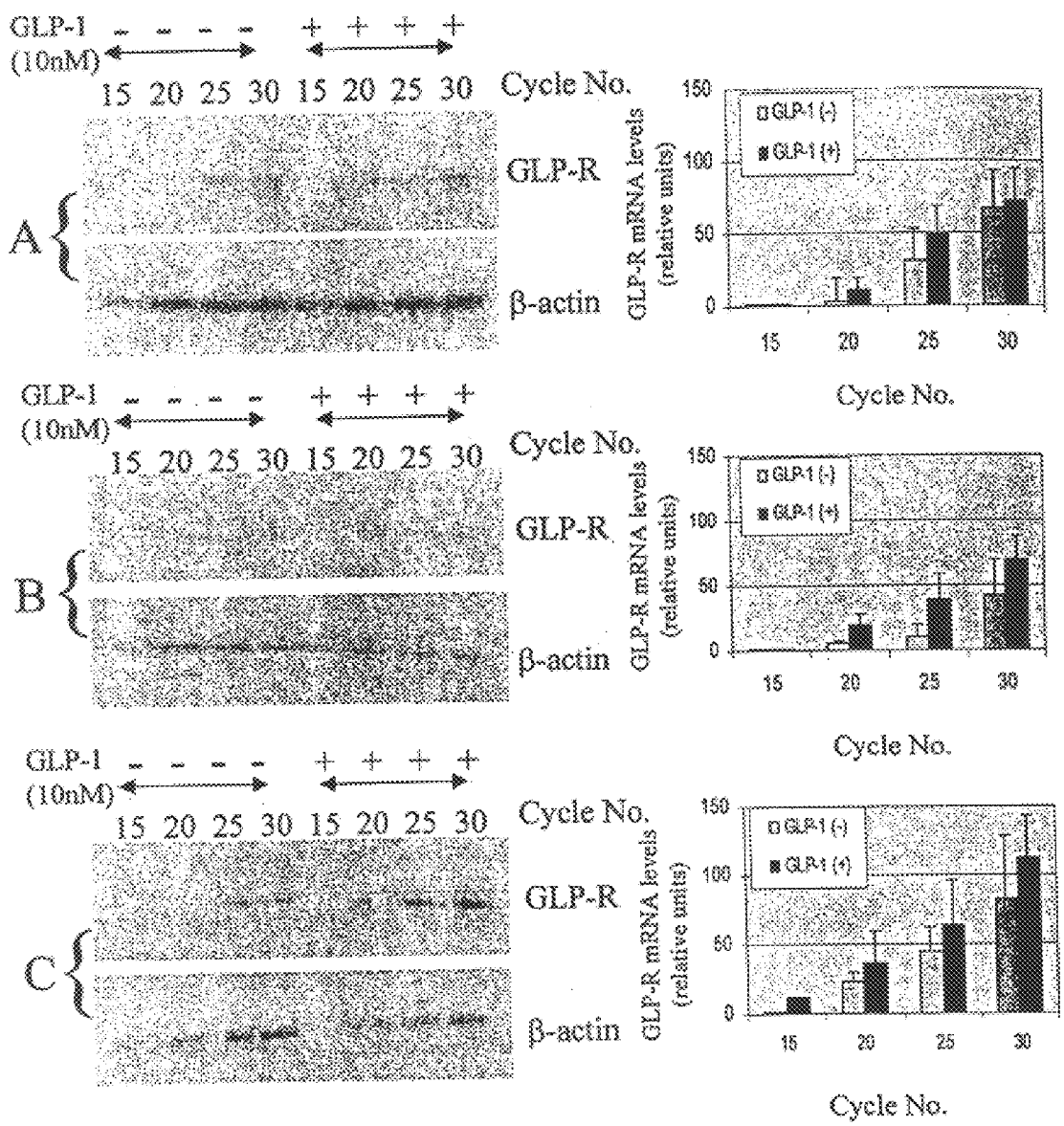

Detection of GLP-R by RT-PCR with gene-specific primers revealed that both ARIP and PANC-1 cells constitutevely (i.e. prior to the treatment with GLP-1 or transfection with the IDX-1 gene) expressed the receptor for GLP-1. Cellular transfection of PANC-1 cells with the IDX-1 gene increased the mRNA level for GLP-R ($p<0.01$ comparing PANC-1/IDX-1 cells vs. either wild-type PANC-1 or ARIP cells, after 25 PCR cycles). Treatment with GLP-1 (10 nM, for 72 h) promoted a further modest increase (no-statistically significant) in GLP-R mRNA levels both in transfected and non-transfected cells (FIG. 9).

Flow Cytometric Analysis

The ability of GLP-1 to promote the differentiation of IDX-1 positive ductal epithelial cells into insulin synthesizing cells was further confirmed by FACS analysis. This procedure was employed to provide a quantitative measure of the ability of GLP-1 to induce the differentiation of insulin-secreting cells.

ARIP cells cultured for 72 hours in the presence of GLP-1 (10 nM) were able to transcribe and translate the insulin gene, such that 72.6% of them reacted with an anti-human insulin antibody, demonstrating that they were able to synthesize insulin (FIG. 10). PANC-1 cells cultured in the presence or absence of GLP-1 showed that only 1.4% of the entire culture population contained insulin in the cytoplasm, a percentage equivalent to the background level of the assay. Stable transfection with human IDX-1, although not capable of inducing cells to synthesize insulin, was sufficient to render them responsive to GLP-1. Transfection with IDX-1 was not able, per se, to differentiate PANC-1 cells into insulin-producing cells, however treatment with GLP-1 (72 h, 10 nM) was able to convert 61.7% of the cultured cells from insulin negative to insulin positive (FIG. 10). FRCS analysis of PANC-1 cells treated with GLP-1 and stained solely with an unspecific isotype-matched FITC-conjugated antibody, without the primary antibody was used as a negative control (FIG. 10).

---

What is claimed is:

1. A cell that exhibits a dose-dependent response of insulin secretion when exposed to glucose, the cell comprising an exocrine pancreatic cell transfected with IDX-1 cDNA and cultured in glucagon-like peptide-1 (GLP-1).

2. The insulin-secreting cell of claim 1, wherein the pancreatic cell is a PANC-1 cell.

3. The insulin-secreting cell of claim 1, wherein the pancreatic cell is selected from the group consisting of A, B, D, and F islet cells, epithelial cells of intralobular ducts, acinar cells, centroacinar cells, and basket cells.

4. The insulin-secreting cell of claim 1, wherein the pancreatic cell is selected from the group consisting of AsPc-1, AR42J, BxPc-3, Capan-1, Capan-2, Colo357, HPAC, HPAF, HPAF-II, Hs766T, human insulinoma cell line, MiaPaCa, MIAPaCa-2, PANC-1, Panc89, QGP-1, S2CP9, and T3M4 cells.

5. The insulin-secreting cell of claim 1, wherein the cell is cultured in 1–20 nM GLP-1.

6. The insulin-secreting cell of claim 5, wherein the cell is cultured in 10 nM GLP-1.

7. The insulin-secreting cell of claim 5, wherein the cell is cultured for 24–72 hours in GLP-1.

8. The insulin-secreting cell of claim 1, wherein the cell is cultured in DMEM medium.

9. The insulin-secreting cell of claim 1, wherein the cell is cultured in at least one supplement selected from the group consisting of fetal calf serum, penicillin, and streptomycin.

10. A method of producing insulin-secreting cells that exhibit a dose-dependent response of insulin secretion when exposed to glucose, comprising:
    transfecting a line of exocrine pancreatic cells with genetic material selected from the group consisting of IDX-1 DNA, IDX-1 cDNA, and IDX-1 mRNA; and
    culturing the cells in glucagon-like peptide-1 (GLP-1).

11. The method according to claim 10, wherein the pancreatic cells comprise a PANC-1 cell line.

12. The method according to claim 10, wherein the pancreatic cells comprise a cell line selected from the group consisting of AsPc-1, AR42J, BxPc-3, Capan-1, Capan-2, Colo357, HPAC, HPAF, HPAF-II, Hs766T, human insulinoma cell line, MiaPaCa, MIAPaCa-2, PANC-1, Panc89, QGP-1, S2CP9, and T3M4 cells.

13. The method according to claim 10, wherein transfecting the cells with genetic material comprises transfecting the cells with IDX-1 cDNA.

14. The method according to claim 13, wherein transfecting the cells with genetic material further comprises transfecting the cells with a pcDNA3 construct comprising wild-type IDX-1 cDNA.

15. The method according to claim 13, wherein transfecting the cells with genetic material further comprises transfecting the cells by a method selected from the group consisting of coprecipitation of DNA with calcium phosphate, lipofection with cationic liposomes, transfection with polyethylenimine, transfection by electroporation, and receptor-mediated endocytosis.

16. The method according to claim 13, the method further comprising selecting cells that are successfully transfected with the genetic material from cells that are not successfully transfected.

17. The method according to claim 16, the method further comprising transfecting the cells with genetic material that encodes aminoglycoside phosphotransferase and culturing the cells in neomycin geneticin sulfate.

18. The method according to claim 16, the method further comprising transfecting the cells with genetic material that encodes hygromycin phosphotransferase and culturing the cells in hygromycin B.

19. The method according to claim 16, the method further comprising transfecting the cells with genetic material that encodes puromycin N-acetyl transferase and culturing the cells in puromycin.

20. The method according to claim 16, the method further comprising transfecting the cells with genetic material that encodes histidinol dehydrogenase and culturing the cells in histidinol.

21. The method according to claim 16, the method further comprising transfecting the cells with genetic material that encodes dihydrofolate reductase and culturing the cells in methotrexate.

22. The method according to claim 10, wherein culturing the cells in GLP-1 comprises culturing the cells in GLP-1 at a concentration of 1–20 nM GLP-1.

23. The method according to claim 10, wherein culturing the cells in GLP-1 comprises culturing the cells in GLP-1 at a concentration of 10 nM GLP-1.

24. The method according to claim 10, wherein culturing the cells in GLP-1 further comprises culturing the cells in GLP-1 for 24–72 hours.

25. The method according to claim 10, wherein culturing the cells in GLP-1 further comprises culturing the cells in GLP-1 at 37° C. under 95% air and 5% $CO_2$.

26. The method according to claim 10, wherein culturing cell in GLP-1 further comprises culturing the cells in DMEM medium.

27. The method according to claim 10, wherein culturing cell in GLP-1 further comprises culturing the cells in at least one supplement selected from the group consisting of fetal calf serum, penicillin, and streptomycin.

28. A method of determining the ability of a drug to stimulate cells that exhibit a dose-dependent response of insulin secretion when exposed to glucose to secrete insulin, comprising:

exposing exocrine pancreatic cells that have been transfected with IDX-1 cDNA and cultured in GLP-1 to the drug; and measuring the amount of insulin secreted by the cells.

29. The method of claim 28, wherein the step of exposing the cells to the drug comprises exposing the cells to a sulfonylurea.

30. The method of claim 28, wherein the step of exposing the cells to the drug comprises exposing the cells to a drug selected from the group consisting of metformin, acarbose, troglitazone, and repaglinide.

* * * * *